United States Patent
Trost et al.

(10) Patent No.: US 6,541,655 B2
(45) Date of Patent: Apr. 1, 2003

(54) CATALYTIC COMPOSITIONS AND METHODS FOR ASYMMETRIC ALLYLIC ALKYLATION

(75) Inventors: Barry M. Trost, Los Altos, CA (US); Iwao Hachiya, Mie (JP)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/949,467

(22) Filed: Sep. 7, 2001

(65) Prior Publication Data

US 2002/0198383 A1 Dec. 26, 2002

Related U.S. Application Data

(60) Continuation-in-part of application No. 09/498,701, filed on Feb. 7, 2000, which is a division of application No. 09/213,395, filed on Dec. 15, 1998, now Pat. No. 6,130,349.
(60) Provisional application No. 60/068,128, filed on Dec. 19, 1997.

(51) Int. Cl.$^7$ ............................................. C07C 69/76
(52) U.S. Cl. .............................. 560/80; 560/81; 560/82; 560/83; 560/9; 560/10; 560/51; 560/53; 560/203; 560/121; 549/427; 549/500; 554/162; 554/163
(58) Field of Search .............................. 560/80, 81, 82, 560/83, 9, 10, 51, 53, 203, 121; 549/509, 427; 554/162, 163

(56) References Cited

U.S. PATENT DOCUMENTS 6,130,349 A1    8/2002    Trost et al.

FOREIGN PATENT DOCUMENTS

WO    WO 99/32225    7/1999

OTHER PUBLICATIONS

Tetrahedron :Asymmetry 6:2023 (1995), Adolfsson et al.*
Malkov, Andrei V., et al., "Asymmetric molybdenum(0)–catalyzed allylic substitution", *Tetrahedron Letters* 42, pp. 509–512, Jan. 15, 2001.

Trost, Barry M., et al., "Ligand Dependence of Molybdenum–Catalyzed Alkylations. Molybdenum–Isonitrile Complexes as a New Class of Highly Reactive Alkylation Catalysts", *J. Am. Chem. Soc. 112*, pp. 9590–9600, 1990.

Faller, J.W. et al., "Reversal of Stereochemical Path in Allylic Alkylations Promoted by Palladium and Molybdenum Complexes", *Organometallics 7*, pp. 1670–1672, 1988.

Lloyd–Jones, Guy C., et al., "Chiral Phosphandihydrooxazoles in Asymmetric Catalysis: Tungsten–Catalyzed Allylic Substitution", *Angew. Chem. Intl. Ed. Engl.*, vol. 34, No. 4, pp. 462–464, 1995.

Trost, Barry M., et al., "Chemoselectivity and Stereocontrol in Molybdenum–Catalyzed Allylic Alkylations", *J. Amer. Chem. Soc. 109*, pp. 1469–1478, 1987.

Trost, Barry M., et al., "Regiochemical Diversity in Allylic Alkylations Via Molybdenum Catalysts", *Tetrahedron*, vol. 43, No. 21, pp. 4817–4840, 1987.

Trost, Barry M., et al., "Asymmetric Ligands for Transition–Metal–Catalyzed Reactions: 2–Diphenylphosphinobenzoyl Derivatives of $C_2$–Symmetric Diols and Diamines", *Angew. Chem. Int. Ed. Engl 31*, No. 2, pp. 228–230, 1992.

Trost, Barry M., et al., "A Modular Approach for Ligand Design for Asymmetric Allylic Alkylations via Enantioselective Palladium–Catalyzed Ionizations", *J. Amer. Chem. Soc. 114*, pp. 9327–9343, 1992.

Trost, Barry, M., et al., "Asymmetric Molybdenum–Catalyzed Alkylations", *J. Amer. Chem. Soc 120*, pp. 1104–1105, 1998.

* cited by examiner

*Primary Examiner*—Samuel Barts
(74) *Attorney, Agent, or Firm*—LeeAnn Gorthey; Perkins Coie LLP

(57) ABSTRACT

Complexes of a selected class of chiral ligands with molybdenum, tungsten or chromium, preferably molybdenum, are effective as catalysts in highly enantioselective and regioselective alkylation of allylic substrates.

15 Claims, 5 Drawing Sheets

IX
 X
 XI
 XII

XIII         XIV         XV

CATALYTIC COMPOSITIONS AND METHODS FOR ASYMMETRIC ALLYLIC ALKYLATION

This application is a continuation-in-part of U.S. Ser. No. 09/498,701, filed Feb. 7, 2000, which is divisional of U.S. Ser. No. 09/213,395, filed Dec. 15, 1998, now U.S. Pat. No. 6,130,349, which claims the priority of U.S. Provisional Ser. No. 60/068,128, filed Dec. 19, 1997, all of which are incorporated herein by reference in their entirety.

This invention was made with government support under National Institutes of Health Grant No. 5R37 GM13598-30 and National Science Foundation Grant No. CHE-9501472. Accordingly, the United States Government has certain rights in this invention.

FIELD OF THE INVENTION

The present invention relates to catalytic methods and compositions for use in highly regioselective and enantioselective alkylations of allylic substrates. Molybdenum, tungsten and chromium complexes of chiral ligands having such catalytic activity, particularly the molybdenum complexes, are described, along with methods for their use.

REFERENCES

Adolfsson, H. and Moberg, C., *Tetrahedron: Asymmetry* 6:2023 (1995).

Dvorak, D. et al., *J. Am. Chem. Soc.* 117:6130 (1995) and references cited therein.

Fenton, R. R. et al., *J. Coord. Chem.* 23:291 (1991).

Godleski, S. A., in "Comprehensive Organic Synthesis," Trost, B. M., Fleming, I., and Semmelhack, M. F., eds.; Permagon Press, Oxford, 1991, Vol. 4, pp 585–662.

Hammen, P. D. et al., *Synth. Commun.* 21:2157 (1991).

Merlic, C. A., Ph.D. Thesis, University of Wisconsin (1988).

Pretot, R. and Pfalz, A., *Angew. Chem. Int. Ed. Engl.* 37: 323 (1998).

Rubio, A. and Liebeskind, L. S., *J. Am. Chem. Soc.* 115: 891 (1993).

Saigo, K. etal., *Bull. Chem. Soc. Japan* 59(3):931 (1986).

Trost, B. M. et al., *J. Am. Chem. Soc.* 109: 2176 (1987).

Trost, B. M. and Hachiya, I., *J. Am. Chem. Soc.* 120:1104 (1998).

Trost, B. M. and Hung, M.-H., *J. Am. Chem. Soc.* 105:7757 (1983).

Trost, B. M. and Lautens, M., *J. Am. Chem. Soc.* 104:5543 (1982).

Trost, B. M. and Lautens, M., *J. Am. Chem. Soc.* 109:1469 (1987).

Trost, B. M. and Lautens, M., *Tetrahedron* 43: 4817 (1987).

Trost, B. M. and Merlic, C. A., *J. Am. Chem. Soc.* 112:9590 (1990).

BACKGROUND OF THE INVENTION

Interest in molybdenum- and tungsten-catalyzed reactions of allyl substrates with nucleophiles has been promoted by the regioselectivity shown by these complexes, as compared to that of palladium complexes. See, for example, for molybdenum, Trost and Merlic, 1990, Rubio and Liebeskind, 1993, Trost and Hachiya, 1998; and for tungsten, Trost and Hung, 1983, and Trost et al., 1987.

Palladium catalyzed reactions generally provide products from attack at the less substituted terminus. This regiochemistry (shown at eq 1, path a in FIG. 1) is particularly favored for alkylation of aryl-substituted allyl systems, even with catalysts having chiral ligands (Godleski, 1991). Molybdenum and tungsten catalysts, on the other hand, generally favor attack at the more substituted terminus (eq 1, path b). Complexes of these metals are also less costly than palladium catalysts.

Products of the type shown in reaction path (b), having high optical purity, find great value as building blocks in the synthesis of biologically useful compounds. A low-cost, versatile, stereoselective catalytic route to such compounds would thus be desirable.

SUMMARY OF THE INVENTION

In one aspect, the invention provides a catalytic organometallic composition, effective to catalyze the enantioselective alkylation of an allyl group bearing a leaving group at an allylic position. The composition comprises a metal atom selected from the group consisting of molybdenum, tungsten, and chromium, which is preferably molybdenum or tungsten and most preferably molybdenum, and coordinated thereto, a chiral ligand $L^1$. The chiral ligand comprises a chiral component derived from a chiral diamine, and having first and second carbon atoms each bearing a binding group —NH—(C=O)—B, wherein:

the above-referenced carbon atoms are connected by a direct bond or by a chain of one to three atoms comprising linkages selected from alkyl, alkyl ether, alkyl amino, and combinations thereof, each group B is independently selected from alkyl, cycloalkyl, heterocycle, aryl, and aralkyl, as defined herein;

at least one group B is a N-heterocyclic or N-heteroaryl group CyN having an $sp^2$ hybridized ring nitrogen atom effective to coordinate to said metal atom, and at least one of the above-referenced carbon atoms is a chiral carbon atom bearing a further substituent effective to create a conformationally biased system containing the carbon atoms and the binding groups.

In preferred embodiments, the substituent (or substituents) on the above-referenced carbon atom(s) are independently selected from aryl, aralkyl, carbocycle, heterocycle, and secondary or tertiary alkyl having 3 or more, preferably 4 or more, carbon atoms. In one such embodiment, the substituents are aryl groups. In another embodiment, where both of the above-referenced carbon atoms are chiral and are adjacent, the substituents on these carbon atoms may together form a ring. This ring is typically a 5- to 7-membered carbocyclic ring, or a 5- to 7-membered heterocyclic ring having 1–3, preferably 1–2, ring atoms selected from oxygen, nitrogen and sulfur, and the remaining ring atoms carbon. It may be fused to one or more additional rings, preferably no more than two, and more preferably one or none. The ring or other substituents, particularly he cyclic substituents, may themselves be substituted with one or more groups selected rom alkyl, alkenyl, aryl, aralkyl, alkoxy, aryloxy, acyl, acyloxy, carboxylic ester, amide, tertiary amine, nitro, and halogen.

In further embodiments, each said group B is a group CyN as defined above, and/or each said carbon atom is a chiral carbon atom bearing a substituent effective to create a conformationally biased system containing said carbon atoms and said binding groups. The carbon atoms are preferably connected by a direct bond.

Examples of the groups B described above as CyN, which may be the same or different on a given ligand, include, but are not limited to, pyridyl, quinolinyl, isoquinolyl, pyrimidyl, triazinyl, tetrazinyl, pyrazinyl, pyrazolyl, triazolyl, tetrazolyl, oxazinyl, oxazolyl, thiazolyl, imidazolyl, benzoxazole, benzimidazole, and dihydro derivatives of the above. N-heteroaryl groups are generally preferred. In one embodiment, at least one group B is a group CyN having an $Sp^2$ hybridized ring nitrogen which is α to a nrng carbon atom which is linked to the carbonyl (C=O) carbon of the binding group (referred to herein as an "α-linked" CyN). Examples of these groups include 2-pyridyl, 2-quinolinyl, 1- or 3-isoquinolyl, 2- or 4-pyrimidyl, 2-triazinyl, 4-tetrazinyl, 2-pyrazinyl, 3- or 5-pyrazolyl, 3- or 5-triazolyl, 2-tetrazolyl, 2-oxazinyl, 2- or 5-oxazolyl, 2- or 5-thiazolyl, 2- or 4-imidazolyl, 2-benzoxazole, 2-benzimidazole, and dihydro derivatives of the above.

The above-referenced carbon atoms of the chiral component are connected by a direct bond or by a chain of one to three atoms comprising linkages selected from alkyl, alkyl ether, alkyl amino, and combinations thereof. Preferably, they are connected by a direct bond, such that the chiral scaffold is derived from a 1,2-diamine. Examples of chiral 1,2-diamines that may be used as chiral scaffolds include 1R,2R-trans-diaminocyclohexane, 1R,2R-trans-diphenyl-1, 2-ethanedi amine, 3R,4R-trans-3,4-diamino-N-benzylpyrrolidine, 1R,2R-trans-diarninocycloheptane, 5R,6R-trans-5,6-diaminoindan, 1S-phenyl-1,2-ethanediamine, and the mirror image counterpart of any of the above. Examples of chiral ligands of the invention include those represented herein as ligands I–XV and their mirror image counterparts.

The catalytic organometallic composition of the invention is the product of a process which comprises contacting, in a suitable solvent, a chiral ligand $L^1$, as defined above, with a complex (also referred to herein as the starting complex or precomplex) of a metal selected from tungsten (0), chromium (0), and molybdenum(0), ligands which form a stable complex with the metal and are displaceable by ligand $L^1$ under the conditions of said contacting. Such ligands include CO, cycloheptatriene, lower alkyl nitrile, and lower alkyl isonitrile. Preferred precomplexes for the preparation of the molybdenum catalysts include $Mo(h^{3-}C_7H_8)(CO)_3$ (cycloheptatriene molybdenum tricarbonyl), $Mo(CO)_3(CH_3CH_2CN)_3$, and $Mo(CO)_6$. Tungsten and molybdenum complexes are preferred, with molybdenum being particularly preferred. Upon such contacting, the complex undergoes a ligand exchange reaction, such that $L^1$ becomes coordinated to the metal atom. The resulting composition is effective to catalyze the enantioselective alkylation of an allyl group bearing a leaving group at its allylic position.

In the above process, the molar ratio of the ligand $L^1$ added to the hexacoordinate precomplex is generally between about 2:1 and about 1:1, and preferably between about 1.1:1 and about 1.5:1.

In another aspect, the invention provides a method of selectively alkylating an allyl group bearing a leaving group at the allylic position, under conditions effective to produce an alkylated product which is enriched in one of the possible isomeric products of such alkylation. The alkylation method comprises reacting the allyl group with an alkylating agent, in the presence of a catalytic amount of an alkylating catalyst. The alkylating catalyst is an organometallic complex having a metal atom selected from the group consisting of molybdenum, tungsten, and chromium, and coordinated thereto, a chiral ligand $L^1$, as defined above. The metal atom is preferably molybdenum or tungsten, and more preferably molybdenum.

In a related aspect, the method comprises reacting such a substrate with an alkylating agent in the presence of a catalytic composition formed by contacting, in a suitable solvent, catalytic amounts of (i) a complex of a metal selected from the group consisting of molybdenum (0), tungsten (0), and chromium (0), having ligands which form a stable complex with the metal and are displaceable by ligand $L^1$ under the conditions of said contacting, and (ii) a chiral ligand $L^1$, as defined above. Such ligands include CO, cycloheptatriene, lower alkyl nitrile, and lower alkyl isonitrile. The mole percent of said catalyst with respect to said substrate is preferably between about 0.5% and about 15%, and more preferably between about 1% and about 10%.

The reaction is carried out under conditions effective to produce an alkylated roduct which is enriched in one of the possible isomeric products of such alkylation. In one aspect, the alkylation is enantioselective, and preferably produces an alkylated product having an enantiomeric excess greater than 75%, preferably greater than 85% and more preferably greater than 95%. In another aspect, when the allyl group is nonsymmetrically substituted at its termini, the alkylation is regioselective, such that said allyl group is alkylated at its more sterically hindered terminus. Preferably, the regioselectivity of alkylation, defined as the ratio of product alkylated at the more sterically hindered terminus to product alkylated at the less sterically hindered terminus, is greater than 3:1, and more preferably greater than 9:1.

Preferred allyl substrates for the reaction are those in which the allyl group is substituted at one terminus with a substituent selected from aryl, heteroaryl, alkenyl, alkynyl, and alkyl. The reaction is especially useful for substrates in which neither allyl terminus is aryl substituted. This includes those in which one terminus is substituted with an alkyl group or with a non-aromatic conjugated polyene or enyne. In another embodiment of the method, where the allyl group has identical non-hydrogen substituents at its termini (with the exception of the leaving group), the alkylation is enantioselective with respect to the new chiral center formed at the alkylated termninus of said allyl group.

The alkylating agent is a preferably a stabilized carbanion, such as a carbanion of the form $EE'RC^- M^+$, where $M^+$ is a positively charged counterion, and each of E and E' is a substituent which stabilizes the carbanion, e.g. an electron-withdrawing substituent selected from keto, carboxylic ester, cyano, and sulfonyl, or an aromatic or heteroaromatic group capable of stabilizing an α-carbanion. Preferably, at least one of E and E' is a carboxylic ester.

In a preferred embodiment of the method, the catalyst is formed in situ by ligand exchange of a soluble molybdenum (0) complex with ligand $L^1$. The complex, as described above, comprises ligands which are effective to form a stable complex with Mo(0) and which are displaceable by ligand $L^1$ under the conditions of the ligand exchange. Preferred ligands include cycloheptatriene, CO, lower alkyl nitrile, and lower alkyl isonitrile.

These and other objects and features of the invention will become more fully apparent when the following detailed description of the invention is read in conjunction with the accompanying drawings.

DETAILED DESCRIPTION OF THE INVENTION

I. Definitions

Figure 1:
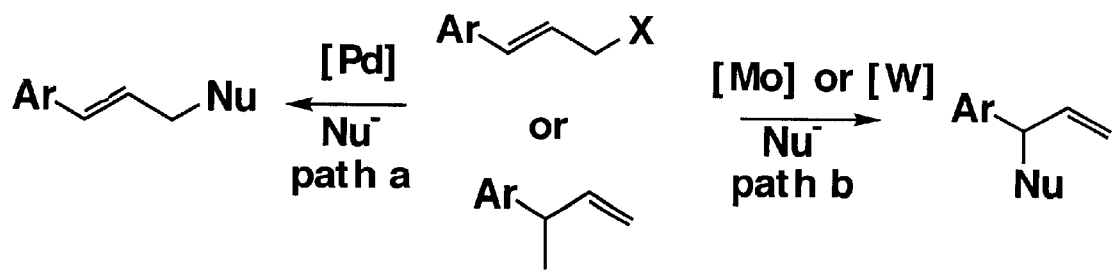
FIG. 1 shows the generally favored regioselectivity of allylic alkylation using palladium catalysts (a) and using molybdenum and tungsten catalysts (b)

The terms below have the following meanings unless indicated otherwise. "Enantiomeric excess" or "e.e." refers to the quantity E1–E2, where E1 is the fraction of a compound having one enantiomeric configuration, and E2 is the fraction having the mirror image configuration.

In an allyl group, that is, a three-carbon moiety having a double bond between carbons 1 and 2 and a single bond between carbons 2 and 3, the "allylic position" is the 3 position, and the "termini" are the 1 and 3 positions.

An "asymmetric" or "enantioselective" alkylation refers to an alkylation reaction which produces one possible enantiomer of an alkylated center in a product in excess over the other enantiomer. A "regioselective" alkylation is one in which, when the allyl group is nonsymmetrically substituted at its termini, alkylation occurs at one terminus in excess over the other. The term "stereoselectivity", as used herein, encompasses enantioselectivity and/or regioselectivity.

A "chiral component", as used herein in reference to chiral ligands used in the catalysts of the invention, refers to a chiral diamine moiety which forms a chiral scaffold to which two binding groups, as defined herein, are linked.

"Alkyl" refers to a fully saturated acyclic monovalent radical containing carbon and hydrogen, which may be branched or a straight chain. Examples of alkyl groups are methyl, ethyl, n-butyl, t-butyl, n-heptyl, and isopropyl. "Cycloalkyl" refers to a fully saturated cyclic monovalent radical containing carbon and hydrogen, which may be further substituted with alkyl. Examples of cycloalkyl groups are cyclopropyl, methyl cyclo-propyl, cyclobutyl, cyclopentyl, ethylcyclopentyl, and cyclohexyl. As used herein, the term generally refers to alkyl groups having 1 to 12, preferably 2 to 6, carbon atoms, or 5 to 7 ring carbons in the case of cycloalkyl.

A "heterocycle" refers to a non-aromatic ring, preferably a 5- to 7-membered ring, whose ring atoms are selected from the group consisting of carbon, nitrogen, oxygen and sulfur and include at least one non-carbon atom (heteroatom). Preferably, the ring atoms include 1 to 3, preferably 1 to 2, heteroatoms and the remainder carbon atoms. Such heterocycles include, for example, pyrrolidine, piperidine, piperazine, and morpholine. An "N-heterocycle" is such a ring containing at least one ring nitrogen atom.

"Aryl" refers to a substituted or unsubstituted monovalent aromatic radical, preferably having a single ring (e.g., phenyl) or two condensed rings (e.g., naphthyl). The term "aryl" includes heteroaryl; that is, aryl groups having one or more nitrogen, oxygen, or sulfur atoms in the ring, such as furan, pyrrole, pyridine, pyrimidine, and indole. "N-heteroaryl" indicates that the group contains at least one ring nitrogen atom. An aryl group may be substituted with one or more substituents, preferably selected from alkyl, alkenyl, aryl, aralkyl, alkoxy, aryloxy, acyl, acyloxy, amide, tertiary amine, nitro, and halogen.

"Aralkyl" refers to an alkyl, preferably lower alkyl ($C_1$ to $C_4$), substituent which is further substituted with an aryl group.

"Acyl" and "acyloxy" refer to groups having the form —C(O)R or —OC(O)R, respectively, where R is an alkyl, aryl, or aralkyl group.

II. Catalysts for Asymmetric Alkylation

The asymmetric catalysts of the invention are complexes of molybdenum, tungsten, or chromium with a chiral ligand as described below. Complexes of molybdenum or tungsten are preferred, with molybdenum being most preferred. In accordance with the invention, such catalysts are effective to catalyze the alkylation of allylic substrates, giving a product which is enriched in one of the possible isomeric products of such alkylation. Specifically, use of the catalysts provides high enantioselectivity and high regioselectivity, as demonstrated below.

A. The Chiral Ligand

The chiral ligand, designated $L^1$, can be described in terms of structural components, which include a chiral component, or "scaffold", and binding components. Exemplary ligands include those designated I–XV herein. A linearized structure of a representative ligand, according to one embodiment of the invention, is given below.

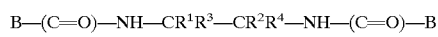

The chiral component, represented by the central portion of the structure, is derived from a chiral diamine. The nitrogen atoms of the diamine are linked to first and second carbon atoms as shown, of which at least one is chiral. Groups B, described further below, are linked to the scaffold via amide linkages containing these nitrogen atoms.

The moieties —NH—(C=O)—B are referred to herein as binding groups. Each group B is independently selected from alkyl, cycloalkyl, heterocycle, aryl, including heteroaryl, and aralkyl, as defined above.

In one embodiment, B is a N-heterocyclic or N-heteroaryl group, represented herein by CyN. The group CyN has an sp hybridized ring nitrogen, and is preferably linked to the carbonyl group (C=O) via a ring carbon atom which is α to (adjacent) this ring nitrogen. Such a group is referred to herein as "α-likked". Examples of such heterocyclic and heteroaryl groups which are α-likked include 2-pyridine, 2- or 4-pyrimidine, 2-pyrazine, 2-triazine, 3- or 5-triazole, 3- or 5-pyrazole, 2-2-pyrazine, 2-4-imidazole, 2- or 5-oxazole, 2- or 5-thiazole, 2-oxazoline, and the like, and multiring structures such as 2-benzoxazole, 2-benzimidazole, 2-quinoline, and 1- or 3-isoquinoline. Also included are dihydro derivatives of these groups, e.g. dihydropyridines, as long as the ring includes an $sp^2$ hybridized ring nitrogen. (Linking of some dihydro derivatives will create a further chiral center, whose stereochemistry must be controlled during synthesis or purification of the ligand.)

Non-α-likked CyN groups (e.g. β-linked groups, which would include, for example, 3-pyridyl, 3-quinolinyl, 4-isoquinolyl, 4-pyrazolyl, 3-oxazinyl, 4-oxazolyl, 4-thiazolyl, and dihydro derivatives of the above) and carbocyclic aryl groups (e.g. phenyl) are additional embodiments of B.

Each group B, particularly cyclic groups, may be substituted with one or more groups selected from alkyl, alkenyl, aryl, aralkyl, alkoxy, aryloxy, acyl, acyloxy, ester, amide, tertiary amine, nitro, or halogen. Cyclic groups may be fused to one or more additional rings, preferably no more than one. Preferably, substituents on the ligand do not include active (acidic) hydrogens, e.g. phenolic groups or primary or secondary amines.

At least one of the carbon atoms of the diamine (chiral scaffold) is a chiral carbon atom and bears a substituent (e.g., $R^1$ in the linearized structure above) which is effective to create a conformationally biased system (i.e., having a conformation which is energetically favored and influenced by the presence of the substituent) containing the two carbon atoms and the binding groups. The extent of conformational bias is such that the chiral ligand is effective in catalyzing the stereoselective (i.e. enantioselective and/or regioselective) alkylation reactions described herein.

Such a substituent (e.g. $R^1$) is preferably selected from aryl, heteroaryl, aralkyl, cycloalkyl, heterocyclyl, and secondary or tertiary alkyl having 3 or more, preferably 4 or more, carbon atoms. Cycloalkyl is preferably cyclopentyl to cycloheptyl, and heterocyclyl is preferably or a 5- to 7-membered heterocyclic ring having 2–3 ring atoms selected from oxygen and nitrogen and the remaining ring atoms carbon. Preferably, such a heterocyclic ring contains one or two heteroatoms. Examples of suitable substituents on the chiral carbon atoms include, but are not limited to, phenyl, pyridyl, benzyl, naphthyl, cyclohexyl, furanyl, pyranyl, isopropyl, t-butyl, and 1-methyl butyl (sec-pentyl). Aryl substituents are preferred, particularly when the ligand includes only one chiral carbon. The substituents themselves, particularly the cyclic substituents, may be further substituted with alkyl, alkenyl, aryl, aralkyl, alkoxy, aryloxy, acyl, acyloxy, amide, tertiary amine, nitro, or halogen. The chiral carbon(s) may be disubstituted, as long as chirality is maintained, but are preferably monosubstituted.

Ligands in which each carbon atom is chiral and bears such a substituent include those in which the chiral carbons are adjacent and their substituents together form a carbocyclic or heterocyclic ring. Preferably, such a ring is a 5- to 7-membered carbocyclic ring, or a 5- to 7-membered heterocyclic ring having 2–3 ring atoms selected from oxygen and nitrogen and the remaining ring atoms carbon. Preferably, such a heterocyclic ring contains one or two heteroatoms. Examples include, but are not limited to, cyclohexane, piperidine, piperazine, pyrrolidine, morpholine, di- or tetrahydrofuran, and di- or tetrahydropyran. $R^1$ and $R^2$, or the ring formed thereby, may be further substituted with one or more groups selected from alkyl, alkenyl, aryl, aralkyl, alkoxy, aryloxy, acyl, acyloxy, amide, tertiary amine, nitro, or halogen. $R^1$ and $R^2$, or the ring formed thereby, may also be fused to one or more additional rings, preferably no more than two, and more preferably one or none. Although the remaining groups on the carbon atoms ($R^3$ and $R^4$) are typically hydrogen, the carbon atoms may also be tetrasubstituted, as long as they remain chiral.

An exemplary chiral diamine for use in preparing ligands of this class is 1R,2R-trans-diaminocyclohexane (see FIG. 2A) or its enantiomer, 1S,2S-trans-diaminocyclohexane, both of which are commercially available. FIGS. 2–3 show additional chiral ligands based on 5- and 7-membered rings. See, for example, ligands XIV and XV, where the chiral scaffold is based on cyclohexanediamine, one group B is 2-pyridyl, and the second group B is phenyl or 3-pyridyl, respectively. Also preferred are diamines having bulky substituents, such as trans-1,2-diamino-1,2-diphenylethane (see e.g. ligand II).

An example of a ligand in which only one of the carbon atoms is chiral (e.g., where $R^2$ and $R^4$ are both hydrogen) is ligand XIII, where $R^1$ is phenyl, $R^2$–$R^4$ are hydrogen, and each group B is 2-pyridyl.

In preferred embodiments, the carbon atoms bearing the binding groups are connected by a direct bond, as in the linearized structure above; that is, the diamine is a 1,2 system. However, chiral components having intervening bonds between these carbon atoms, e.g. 1,3-, 1,4-, or 1,5-systems, can also be effective. In such cases, the carbon atoms are connected by a chain of one to three atoms comprising linkages selected from alkyl (carbon-carbon) alkyl ether (carbon-oxygen), alkyl amino (carbon-nitrogen), or a combination thereof. In such ligands, each group B is preferably an α-linked CyN as described above.

A distinctive type of chiral ligand is that in which $R^1$ and $R^2$ are naphthyl groups which are linked to form a 1,1'-binaphthyl system (or analogous multinuclear systems). In such cases, for use in the present catalysts, the amine and/or alcohol groups of the chiral component are at the 2 and 2'-positions. Although these positions are not chiral centers in the conventional sense (i.e. they do not have four different substituents), the naphthyl groups form a helical system possessing what is termed axial chirality.

B. Preparation of the Chiral Ligand

Many chiral diamines are commercially available. Such compounds can also be prepared from naturally occurring chiral precursors, e.g. amino acids, saccharides, tartrates, etc., using established synthetic procedures. Chiral compounds may also be prepared from achiral or racemic precursors using known synthetic methods having high stereoselectivity. The development of such methods has been an active field of research for many years and is the subject of many articles, books and treatises. In many cases, particularly for compounds which can form crystalline salts, e.g. many amines, optical resolution can provide compounds of high optical purity. For example, optical resolution of racemic 1,2-diphenylethanediamine gave the (+) and (−) enantiomers in over 99% and 97% optical purity, respectively (Saigo et al., 1986), and racemic trans-1,2-diaminocyclohexane was resolved to >99% optical purity via the lactic acid salt (Imaoka, 1995). Chromatography of racemic compounds on chiral supports has also been found useful.

Chiral ligands as described above can be conveniently prepared by condensation reaction of the chiral diamine with a suitable carboxylic acid derivative of the component or components represented by B. As shown in the preparation of ligands XIV and XV described in the Examples, ligands having two different binding groups can be prepared by using differentially activated or protected precursors (Example 24) or simply by separating the desired compound from the side product symmetrical compounds (Example 23).

C. Preparation of Catalysts

The chiral catalyst is readily generated by ligand exchange of the ligand $L^1$ with a soluble complex of Mo(0), W(0), or Cr(0), where the molybdenum and tungsten complexes are preferred, and molybdenum particularly preferred. Suitable starting complexes are those having ligands which stabilize the starting complex, but are displacable by the chiral ligand $L^1$ under mild conditions. Such ligands include, for example, cycloheptatriene, carbon monoxide, lower alkyl nitriles or isonitriles, or combinations thereof. Particularly preferred starting complexes are cycloheptatriene molybdenum tricarbonyl (Mo(h3-$C_7H_8$)(CO)$_3$), molybdenum hexacarbonyl (Mo(CO)$_6$) and molybdenum tris(propionitrile) triscarbonyl ($CH_3CH_2CN$)$_3$Mo(CO)$_3$.

The ligand $L^1$ and starting complex are stirred in an inert, nonprotic and noncomplexing solvent, in an inert atmosphere, e.g. dry nitrogen or argon, preferably in a molar ratio of about 1:1 to about 1:2, more preferably in the range of about 1:1.1 to about 1:1.5. In general, a larger scale preparation will call for a smaller excess of ligand $L^1$ over starting metal complex. Suitable solvents include THF, diethyl ether, other hydrocarbon ethers such as dioxane; toluene, other hydrocarbon solvents such as benzene or petroleum ether; chlorinated solvents such as chloroform or dichloromethane, or mixtures thereof. Preferred solvents are hydrocarbons, hydrocarbon ethers, and mixtures thereof.

For the experiments described below, a 1:1.5 ratio of $(CH_3CH_2CN)_3Mo(CO)_3$ to ligand $L^1$ was typically used in preparing the catalyst, and the reaction was carried out at room temperature or in refluxing THF (about 65° C.). The catalytic complexes may be thus generated and then used in situ for alkylation, as described in the Examples below.

III. Asymmetric Allylic Alkylation Method

A. General Procedure

The asymmetric alkylation of the invention is carried out by contacting an allylic substrate and an alkylating agent with a solution containing a catalytic amount of a chiral catalyst as described above. In a preferred embodiment, the catalyst is generated in situ by reaction of a chiral ligand $L^1$ with a soluble starting complex, as described above. Generation of the catalyst is followed by addition of the alkylating agent and the allylic substrate. In other embodiments of the method, the catalyst may be added to the substrate and alkylating agent.

All of these operations are carried out in a suitable aprotic and non-complexing solvent, such as, for example, THF, diethyl ether, other hydrocarbon ethers such as dioxane; toluene, other hydrocarbon solvents such as benzene or petroleum ether; chlorinated solvents such as chloroform or dichloromethane, or a mixture thereof, in an inert atmosphere, e.g. dry nitrogen or argon. Preferred solvents are hydrocarbons, hydrocarbon ethers, and mixtures thereof. The reaction proceeds well both at room temperature and in refluxing THF (65° C.), with greater selectivities and longer reaction times typically resulting at lower temperatures, as shown, for example, in Table 1. A mixture of THF and toluene also gave excellent results. Optimum reaction time and temperature will vary based on factors such as the structure of the substrate, the level of catalyst, and the degree of selectivity desired, and can be determined by one of skill in the art using routine experimentation.

The catalyst is generally effective at levels of about 15 mole percent or less, with respect to the target allyl group. Preferred levels are in the range of about 0.5 to 15 mole percent, and more preferably 1 to 10 mole percent. Larger amounts of catalyst may be used for less reactive ligands and/or substrates.

The alkylating agent (nucleophile) is a preferably a stabilized carbanion, such as a carbanion of the form EE'RC$^-$ M$^+$, where M$^+$ is a positively charged counterion, and each of E and E' is a substituent which stabilizes the carbanion, e.g. an electron-withdrawing substituent selected from keto, carboxylic ester, cyano, and sulfonyl, or an aromatic or heteroaromatic group capable of stabilizing an α-carbanion. Preferably, at least one of E and E' is a carboxylic ester. Preferred nucleophiles include malonates, β-keto esters and β-cyano esters. Alkylating agents containing alkyl and allylic substitution at the attacking carbon were found to be effective (Table 1, lines 8–14). Reaction with other nucleophilic species, such as oxygen- or nitrogen-based nucleophiles, is also contemplated.

The substrate is a compound containing an allyl group which bears a leaving group at the allylic position. Alkylation of such a substrate according to the present method, using the catalytic complex described herein, is effective to produce an alkylated product which is enriched in one of the possible isomeric products of such alkylation. The benefits of the invention are most clearly seen with non-symmetrically substituted allyl groups. By "non-symmetrically substituted" is meant that the allyl group contains different groups (not considering the leaving group) at its termini, that is, at the 1 and 3 positions, where the 3 position is the allylic position. In such cases, both high regioselectivity and enantioselectivity are demonstrated, as discussed below.

The catalytic compositions and methods are also useful for enantioselective alkylation of symmetrically substituted allyl groups, that is, where the 1 and 3 positions have identical substituents, with the exception of the leaving group. A simple example of such a substrate is cyclopentene having a leaving group at the 3 position.

Figure 4:
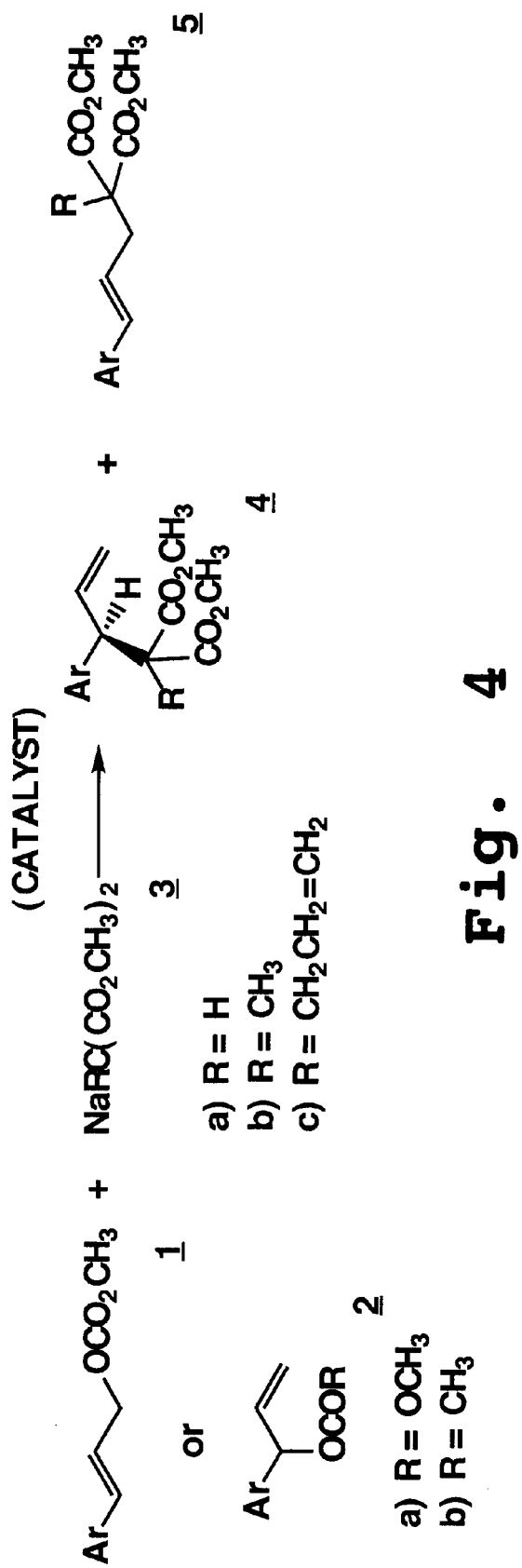
FIG. 4 shows the reaction of an allylic substrate with an alkylating agent, and the two possible products, formed by alkylation at the different termini of the allyl group.

FIG. 4 shows representative non-symmetrically substituted substrates 1 and 2, where the leaving group is a carbonate or acetate. These can be represented more generally by structures R'—CH=CH—CR"H—X (1) or R'—CHX—CH=CR"H (2), where X is a leaving group, and R' and R" are substituents, such as, for example, alkyl, alkenyl, aryl, alkynyl, or heteroaryl. Preferred substrates are those in which the more highly substituted terminus is remote from the leaving group, i.e. 1 as opposed to 2, although good results are also obtained with the latter type of substrate, as shown, for example, in Table 1. Especially favorable substrates are those of structure 1 in which R' is aryl, heteroaryl, or alkenyl, that is, in which R' forms a conjugated system with the allylic double bond. R" is preferably hydrogen, although it may be a substituent.

A very useful feature of the alkylation catalyst and method is the high regioselectivity favoring the more highly substituted terminus of the allyl group, as shown by the data presented herein. The reactions outlined in Table 1, for example, consistently gave regioselectivities of at least 83% (a 5:1 product ratio), and selectivities of about 97% (a 32:1 ratio), or greater, were common.

One general procedure for the reaction, using THF as solvent, is described in Example 1 below. This process was used, with variations in reaction time and temperature, in the alkylation of various substrates with a series of diethyl malonates, using chiral ligand I, to give the results shown in Table 1. All reactions were performed with 10 mol % $(C_2H_5CN)_3Mo(CO)_3$, 15 mol % I in THF at 0.1 M substrate. Values for e.e. were determined by chiral HPLC. In this Table, and others throughout this document, yields not in parenthesis are isolated yields; yields in parentheses are based upon recovered starting material. Typically, tatios of regioisomers were determined by $^1H$ NMR, and e.e. by chiral HPLC, or by comparison to literature values.

In a typical reaction (entry 1), approximately 10 mol % of chiral molybdenum catalyst (based on the starting Mo complex) incorporating chiral ligand I was used in the alkylation of 1 (FIG. 4) with dimethyl sodiomalonate (3, R=H). An 88% yield of a 97:3 ratio of 4:5 (Ar=Ph, R=H) was obtained, with 4 having an e.e. of 99%. When the reaction was carried out at room temperature (entry 2) rather than at reflux, a good yield was still obtained, with somewhat improved regioselectivity and a similarly high e.e.

TABLE 1

Mo Catalyzed Asymmetric Allylic Alkylations

| | 1 or 2 Ar | 3 R | T, °C. | Time, hrs | Yield, % | Ratio 4:5 | ee of 4 |
|---|---|---|---|---|---|---|---|
| 1 | 1, Ph | H | reflux | 3 | 88 | 32:1 | 99 |
| 2 | 1, Ph | H | r.t. | 3 | 70 (90) | 49:1 | 99 |
| 3 | 2a, Ph | H | reflux | 3 | 70 | 13:1 | 92 |
| 4 | 2a, Ph | H | r.t. | 3 | 61 (68) | 32:1 | 97 |
| 5 | 2a, 2-thienyl | H | reflux | 2 | 78 | 19:1 | 88 |
| 6 | 2a, 2-pyridyl | H | reflux | 2 | 69 (82) | 8:1 | 96 |
| 7 | 2a, 1-naphthyl | H | reflux | 2 | 82 | 99:1 | 87 |
| 8 | 1, Ph | $CH_3$ | reflux | 4 | 67 | 24:1 | 98 |
| 9 | 1, 2-furyl | $CH_3$ | reflux | 2 | 71 | 32:1 | 97 |
| 10 | 2b, 2-furyl | $CH_3$ | reflux | 2 | 65 | 32:1 | 87 |
| 11 | 2b, 2-furyl | $CH_3$ | r.t. | 18 | 54 | 99:1 | 95 |
| 12 | 2a, 2-pyridyl | $CH_3$ | reflux | 2 | 71 | 5:1 | 94 |
| 13 | 2a, 2-thienyl | $CH_3$ | reflux | 2 | 71 | 13:1 | 75 |
| 14 | 2b, 2-furyl | $CH_2CH=CH_2$ | r.t. | 12 | 50 | 99:1 | 98 |

Entries 5–7 show corresponding results obtained upon variation of the aromatic ring in the substrate. An electron rich thiophene ring (entry 5), an electron deficient pyridine ring (entry 6), and a bulkier naphthalene substrate (entry 7) all gave good yields and selectivities.

Increasing the steric bulk of the nucleophile by using alkylating agent 3b (FIG. 4) gave similar excellent results with both carbocyclic and heterocyclic substrates (entries 8–12). Only in the case of the thiophene substrate was there some deterioration of the e.e. (75%) for the product (entry 13), although no attempt was made to optimize this reaction. The regioselectivity was still good (about 93%, or a 13:1 product ratio).

When the steric bulk of the alkylating agent was increased further, by using the allylmalonate nucleophile 3c, the regio- and enantio-selectivities were still excellent (entry 14). For the furan substrate bearing the leaving group at the secondary carbon, the acetate 2b, rather than the carbonate 2a, was employed.

The corresponding tungsten catalyst employing ligand I was also found to give high e.e.'s, but gave lower yields and required higher concentrations to give regioselectivities comparable to the molybdenum catalyst. When the reaction in entry 1 was conducted with the tungsten catalyst, generated by stirring a 1:1.5 mixture of $(C_2H_5CN)_3W(CO)_3$ ligand I in THF at 60° C., a modest yield of a 19:1 ratio of 4:5 (Ar=Ph, R=H), where 4 had an ee of 98%, was observed. Increasing the catalyst to 15 mol % increased the yield to 55% and the 4:5 ratio to 49:1, with 4 still having 98% ee.

B. Variation of Chiral Ligand

Figure 2A:
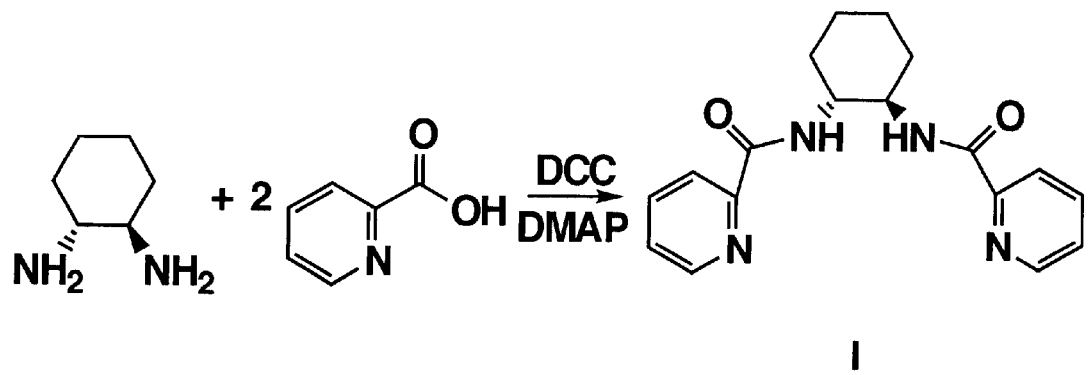
FIGS. 2A–2D show the preparation of several representative chiral ligands which may be employed in the chiral molybdenum catalyst of the invention.
Figure 2B:
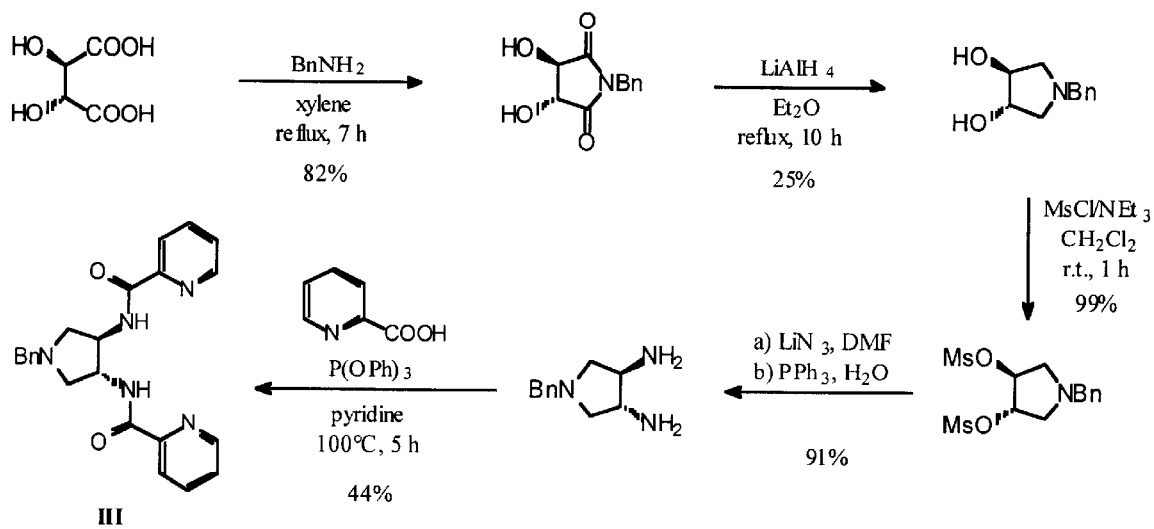
Figure 3A:
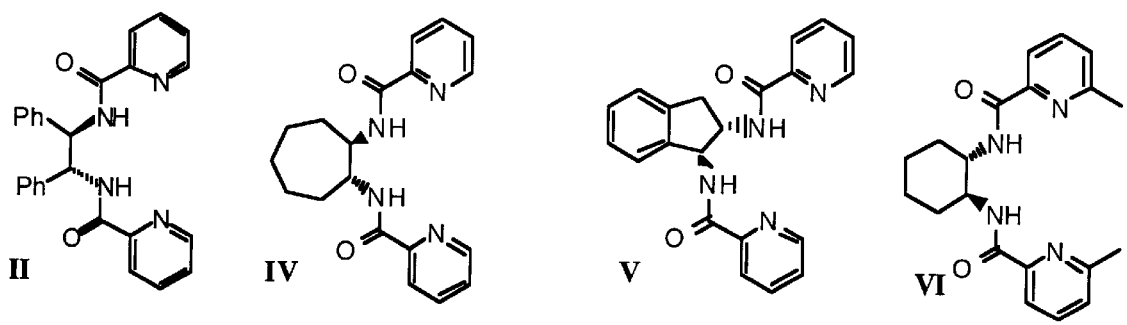
FIGS. 3A–C show additional examples of chiral ligands.

Table 2 shows the results of the Mo-catalyzed alkylation reaction of methyl cin-namyl carbonate using dimethylmalonate as the alkylating agent and catalysts prepared from ligands II and III (based on diphenylethane and pyrrolidine, respectively), shown in FIGS. 2B and 3A. Both ligands gave good selectivity, as shown in the Table.

TABLE 2

Alkylation of Me cinnamyl carbonate with ligands II–III

| Entry | ligand | solvent | temp. [° C.] | time [h] | yield (a + b) | ratio (a:b) | ee [%] |
|---|---|---|---|---|---|---|---|
| 1 | III | THF | 70 | 18 | 40(55) | 82:18 | 94 |
| 2 | II | THF | 70 | 8 | 74(89) | 92:8 | 98 |
| 3 | III | toluene/THF | 90 | 8 | 76(98) | 89:11 | 94 |
| 4 | II | toluene/THF | 90 | 3 | 95 | 95:5 | 99 |
| 5 | II | toluene/THF | 90 | 20 | 46 | 70:30 | 86 |

All reactions were performed in the presence of 0.1 eq $Mo(CO)_3(EtCN)_3$, 0.15 eq ligand, 1.0 eq carbonate, 2.2 eq dimethylmalonate and 2.0 eq NaH (≈0.1 molar), with the exception of entry 5, where only 5 mol % $(EtCN)_3Mo(CO)_3$ was used. Regioselectivity was determined by $^1H$ NMR spectroscopy, and e.e. was determined by enantioselective HPLC. Assignment of the absolute stereochemistry of the major enantiomer as S is based upon comparison of the optical rotation with literature values.

The use of toluene/THF 1:1 as solvent was found to give excellent results. In the case of the pyrrolidine ligand III, the yield and regioselectivity improved and enantioselectivity was still high (entry 3). With the diphenyl ligand II, the reaction was complete after 3 hours, and the product was isolated in 95% yield with excellent regio-(95:5) and enantioselectivity (99% ee) (entry 4). In using this solvent system, the catalyst generally is prepared in toluene (60° C., 1 h), and the substrate and alkylating agent added as a solution in THF (see Example 2).

Figure 2C:
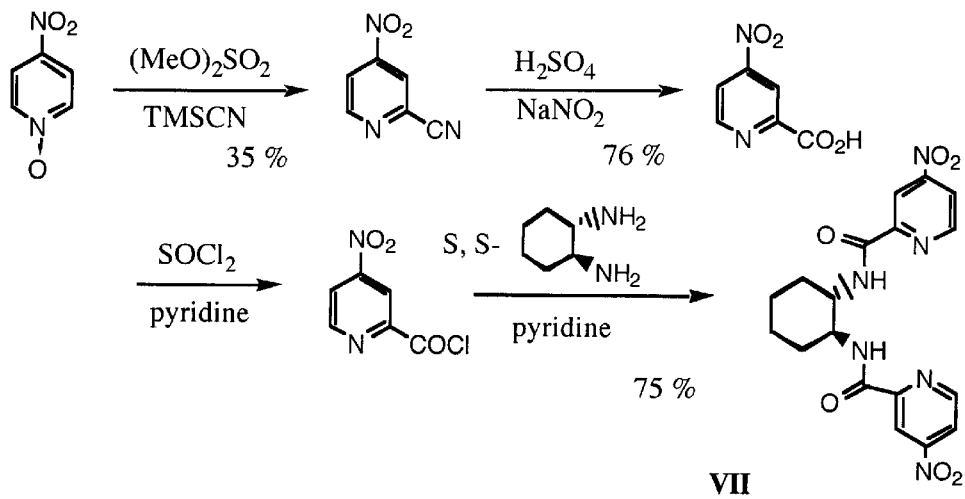
Figure 2D:
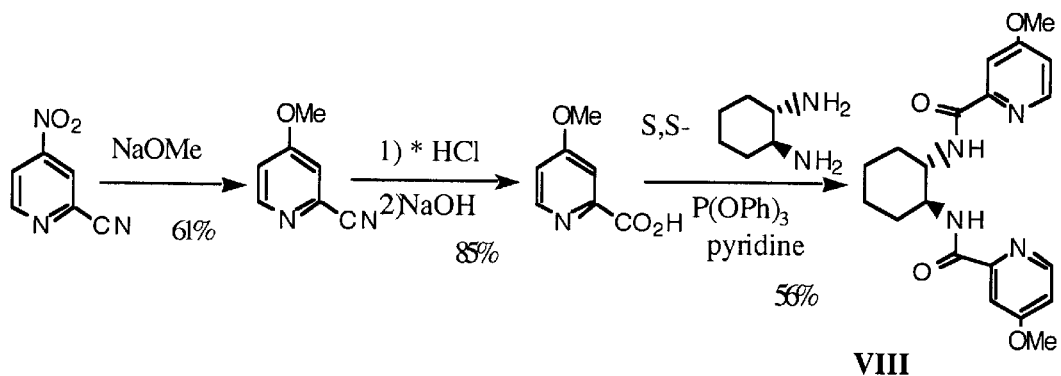

Table 3 shows the reaction of several substrates with malonate using catalysts formed from ligands IV–VIII, shown in FIGS. 2C–D and 3A. Thiophene and naphthalene derivatives were chosen as substrates since they were known to give less than optimum selectivity with the cyclohexyl ligand I.

TABLE 3

Alkylations employing chiral ligands IV–VIII

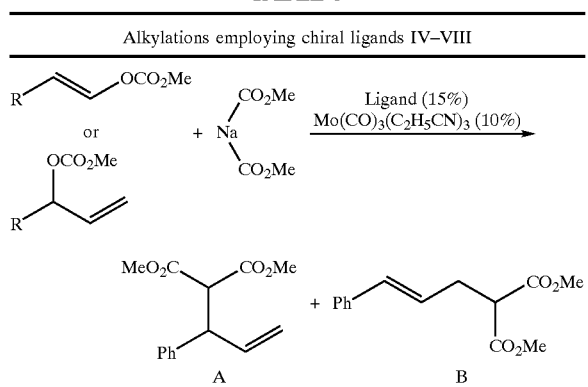

| Substrate | Ligand | Solvent | Temp, °C. | Time, h | Yield, % | A/B | e.e. of A, % |
|---|---|---|---|---|---|---|---|
| R = Ph (upper structure) | IV | THF | 65 | 8 | 74 | 34/1 | 99 |
|  | V | THF | 65 | 18 | 63 | 4.6/1 | 87 |
|  |  |  |  |  | (66) |  |  |
| R = 2-thiophenyl (lower structure) | IV | THF | 65 | 4.5 | 78 | 16/1 | 92 |
|  | IV | THF/toluene | 90 | 1.5 | 87 | 9.5/1 | 82 |
|  | VI | THF | 65 | 18 | 73 | 6.4/1 | 77 |
|  | VII | THF | RT | 47 | 29 (34) | 4.4/1 | 68 |
|  | VIII | THF | 65 | 3 | 83 | 12.7/1 | 84 |
| R = 1-naphthyl (lower structure) | IV | THF | 65 | 5 | 78 | 28.5/1 | 85 |
|  | VI | THF | 65 | 9 | 55 (72) | 12.5/1 | 79 |

Cycloheptyl ligand IV gave similar selectivity to that of the cyclohexyl ligand I, although reaction times were generally longer. Of the remaining ligands in this group, cyclohexyl ligand VIII, having methoxy-substituted pyridyl binding groups, gave the best selectivity and the shortest reaction times.

A molybdenum catalyst prepared as described above and having a 2-quinolinyl group in place of one of the 2-pyridyl groups of ligand I (not pictured) was found to give enantioselectivities similar to those obtained with ligand I, although reaction rates were generally slower.

Figure 3B:
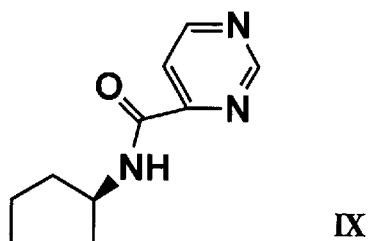
Figure 3B:
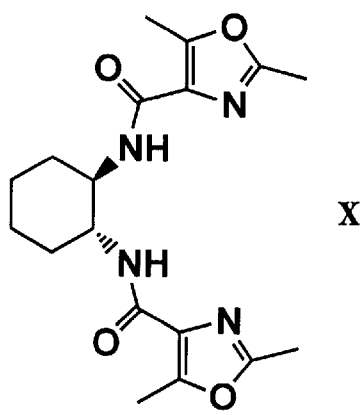
Figure 3B:
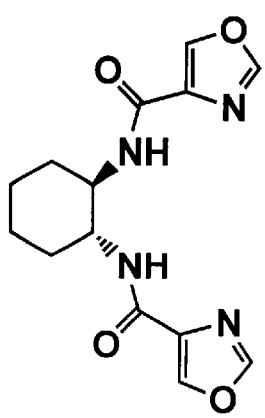
Figure 3B:
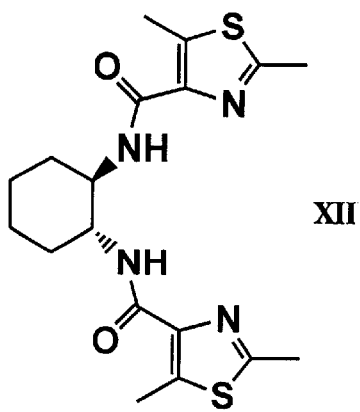

Results are shown below for ligands in which group B, as described above, is selected from a variety of other α-linked CyN type binding groups, including 5-membered rings, as shown in FIG. 3B. In ligand IX, the pyridine rings of ligand I are replaced by 4-pyrimidine rings. Reactions employing this ligand, in accordance with the general procedure, are shown in Table 4.

TABLE 4

Alkylation reactions employing ligand IX

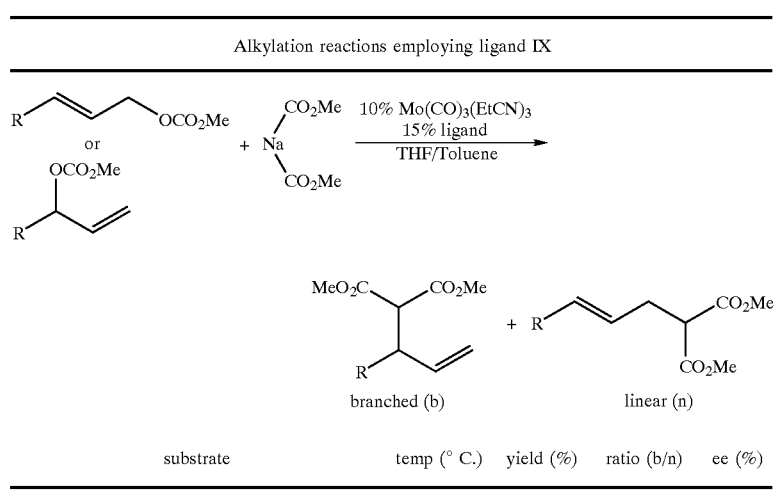

| substrate | temp (° C.) | yield (%) | ratio (b/n) | ee (%) |
|---|---|---|---|---|
| MeO-aryl-OCO₂Me (3,4-dimethoxy cinnamyl) | 85 | 81.5 | 92/8 | 99 |

TABLE 4-continued

Alkylation reactions employing ligand IX

| structure | | | | |
|---|---|---|---|---|
| (CH3)2C=CH-CH=CH-CH2-OCO2Me | 90 | 94 | 94/6 | 91 |
| cyclopentenyl-CH(OCO2Me)-CH=CH2 | 90 | 88 | 93/7 | 86 |

Ligands having various 5-membered heterocyclic rings as groups B were also prepared. In ligands X–XII (FIG. 3B), the 2-pyridyl groups of ligand I are replaced by 2,5-dimethyl-4-oxazole, 4-oxazole, and 2,5-dimethyl-4-thiazole, respectively. Reactions were run in THF using the standard procedure, employing 0.05 mmol Mo complex $C_7H_8Mo(CO)_3$, 0.075 mmol ligand, 1.0 mmol sodiomalonate and 0.5 mmol substrate (methyl cinnamyl carbonate). The reactions were carried out at 25–60° C. for 16 hrs. Results are shown in Table 5. Yields, which were not optimized, were modest (possibly due to contamination and deactivation of the catalyst), but enantioselectivity and regioselectivity (as determined by $^1$H NMR) were excellent.

TABLE 5

Alkylation of methyl cinnamyl carbonate employing ligands X–XII

| ligand | temp (° C.) | yield | ratio (br/lin) | ee (%) |
|---|---|---|---|---|
| X | 25 | 55 | 33:1 | 99 |
| X | 40 | 60 | 34:1 | 99 |
| XI | 60 | 23 (36) | 21:1 | 99 |
| XII | 25 | 20 (30) | 100:1 | 99 |

The reaction scheme below illustrates the effectiveness of a catalyst employing the ligand XIV (FIG. 3C), which has one 2-picolinamide and one benzamide binding group (i.e. one group B is 2-pyridyl and one is phenyl).

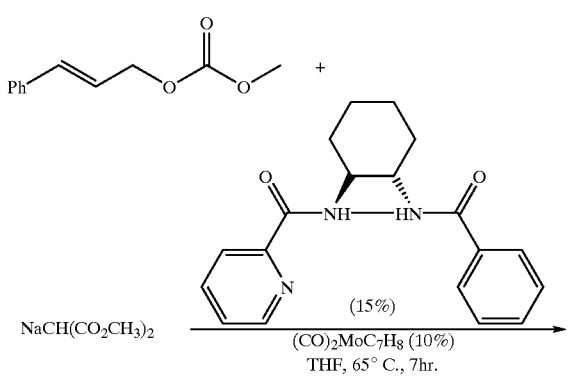

-continued

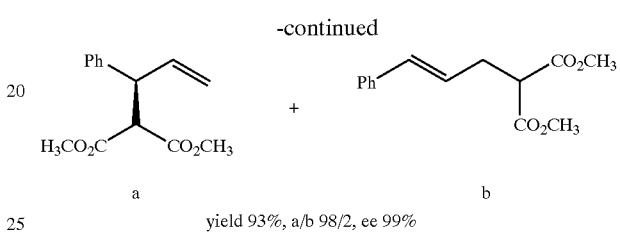

yield 93%, a/b 98/2, ee 99%

A similar reaction employing ligand XV, which has one 2-picolinamide (B=2-pyridyl) and one 3-picolinamide (B=3-pyridyl) binding group, was also successful, giving a 46:1 ratio of branched to linear product in 6 hrs. The branched product had a very high e.e. of 99%.

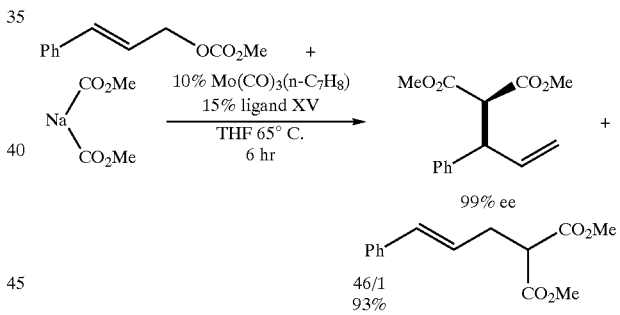

Figure 3C:
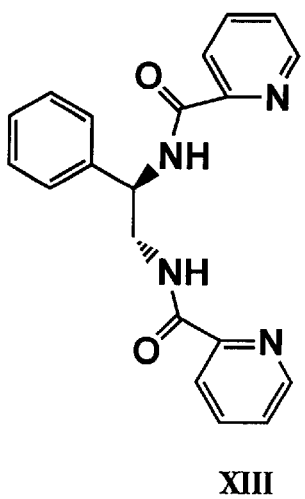
Figure 3C:
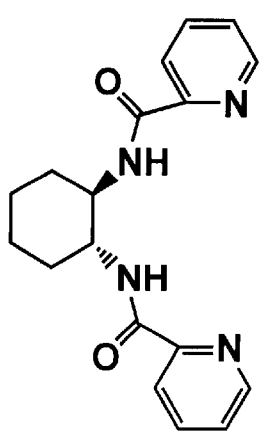
Figure 3C:
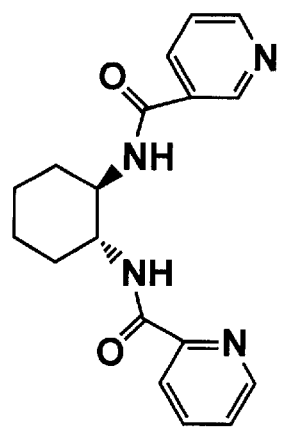

A similar reaction was conducted employing ligand XIII, also shown in FIG. 3C, which has two 2-picolinamide binding groups (B=2-pyridyl) on a chiral scaffold having only one chiral carbon, substituted with phenyl. This reaction, shown in the scheme below, where Ar=3,4-dimethoxyphenyl (2 eq substrate), gave a 90% yield of alkylation product, in an 89/11 ratio of branched to linear product (a/b), after 2 hrs at reflux. The branched product a had an e.e. of 90%.

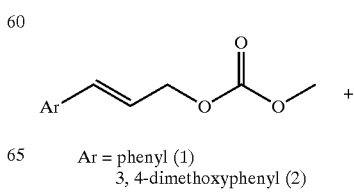

Ar = phenyl (1)
3, 4-dimethoxyphenyl (2)

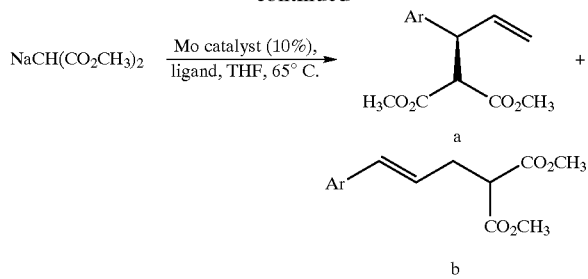

C. Substrate

C1. Aromatic Polyenes

The alkylation of a variety of carbonate substrates using the diphenyl ligand II in toluene/THF 1:1 is shown in Table 6. All reactions were performed in the presence of 0.1 equiv $Mo(CO)_3(EtCN)_3$, 0.15 equiv ligand II, 2.2 equiv dimethylmalonate and 2.0 equiv sodium hydride in toluene/THF 1:1, according to the general procedure of Example 2.

The 2-furyl derivative 6 was alkylated in 71% yield with excellent regio-(95:5) and enantioselectivity (98%) (entry 1). Of this group, the best regioselectivity (98:2) was obtained with the 1-naphthyl carbonate 7, which was alkylated obtained in 91% yield, giving an enantiomeric excess of 87% (entry 2).

The diene system 8 (entry 3) also gave good results, proceeding in 3 hours to give excellent (95%) yield with good regioselectivity (12a/12b 86:14) and excellent enantioselectivity (98% ee). The $^1$H NMR spectra of the isolated product showed no traces of the product derived from alkylation at C5.

The aromatic triene substrate 9 (entry 4) was also converted with high enantio-selectivity (97% ee), although the turnover was somewhat lower. As in the case of substrate 8, this reaction proceeded with high regioselectivity, in the sense that no other alkylation products (i.e. derived from alkylation at C5 or C7), nor the corresponding cis isomer, were detected by $^1$H NMR. Furthermore, the linear product 13b was formed almost exclusively as the all-trans isomer.

TABLE 6

Asymmetric Mo-catalyzed alkylation with diphenyl ligand II

| entry | substrate | time [h] | R = | yield (a + b) | ratio (a:b) | ee [%] |
|---|---|---|---|---|---|---|
| 1 | 6 (furyl carbonate) | 10 | 2-furyl (10) | 71(89) | 95:5 | 98 |
| 2 | 7 (1-naphthyl carbonate) | 8 | 1-naphthyl (11) | 91 | 98:2 | 87 |
| 3 | 8 (cinnamyl diene carbonate) | 3 | styryl (12) | 95 | 86:14 | 98 |
| 4 | 9 (cinnamyl triene carbonate) | 4 | dienyl-phenyl (13) | 58(92) | 84:16 | 97 |

C2. Non-aromatic substrates

Reactions with conjugated polyenes and enynes as substrates were very successful. Reaction of several diene substrates is shown in Table 7.

All reactions were performed in the presence of 0.1 eq.catalyst, 0.15 eq. ligand, 1.0 eq. substrate, 2.2 eq. dimethylmalonate and 2.0 eq. NaH (≈0.1 M), with the exception of entry 7, where 20 mol % catalyst and 30 mol % ligand I were used.

Excellent results were obtained with the diene substrates 14 and 15, using either the cyclohexyl ligand I (entries 1–2) or the diphenyl ligand IV (entry 3). Substrates 16–18 (entries 4–6) were also alkylated in high yields and with good regioselectivities (>9:1), although the enantiomeric excesses were somewhat lower. Alkylation of the heterocyclic non-aromatic dihydropyran carbonate 19 was also successful (entry 7), although a larger amount of catalyst (20 mol %)

TABLE 7

Asymmetric Mo-catalyzed alkylation of non-aromatic diene substrates.

| entry | substrate | time [h] | R = | yield (a + b) | ratio (a:b) | ee [%] |
|---|---|---|---|---|---|---|
| 1 | 14 | 3 | (cyclohexenyl) | 91 | 92:8 | 94 |
| 2 | 15 | 3 | | 89(94) | 98:2 | 98 |
| 3 | 15 | 6 | | 87(95) | 94:6 | 97 |
| 4 | 16 | 3 | | 81(89) | 98:11 | ≈80 |
| 5 | 17 | 2 | | 94 | 92:8 | 87 |
| 6 | 18 | 2 | | 96 | 94:6 | 86 |
| 7[f] | 19 | 1.5 | | 93 | 93:7 | 96 | was required for the reaction to proceed at an acceptable rate.

Substrate 18 was alkylated using the present method within 2 h in 96% yield, with very good regioselectivity (94:6) and with an enantiomeric excess of 86%. In comparison, using the Pd catalyzed method of Prétot et al. (1998), the allylic regioisomer of the same carbonate 18 was alkylated in 75% yield, with much lower regio- and enantioselectivity (75:25 and 51% ee, respectively).

Triene systems such as carbonates 26 or 27 were alkylated in good yields and excellent regio- and enantioselectivities (Table 8). In each case, only 10 mol % catalyst was required, and only one branched isomer (28a and 29a) was obtained. As in the case of the aromatic triene substrate 13, alkylation at C5 or C7 was not observed by $^1$H NMR spectroscopy.

-continued

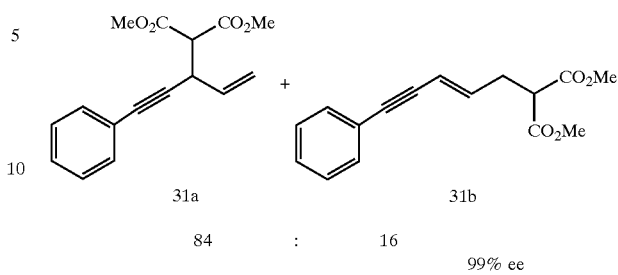

31a : 31b
84 : 16
99% ee

With the non-aromatic alkyne 32, the turnover was somewhat lower (Table 9, entry 1). Increasing the amount of

TABLE 8

Asymmetric Mo-catalyzed alkylation of non-aromatic triene substrates.

| entry | substrate | time [h] | R = | yield (a + b) | ratio (a:b) | ee [%] |
|---|---|---|---|---|---|---|
| 1 | 26 | 2 | (cyclohexenyl-CH=CH-) | 70(79) | 92:8 | 97 |
| 2 | 27 | 3 | (CH3-CH=CH-CH=CH-) | 81(85) | 91:9 | 98 |

The aromatic alkyne substrate 30, below, was alkylated with 10 mol % catalyst in high yield and with good regio- (84:16) and excellent enantioselectivity (99% ee). In contrast to these results, Pd-catalyzed reactions of such substrates were in many cases poorly stereoselective and produced cis/trans mixtures. For example, Pd(0)-catalyzed alkylation of carbonate 30 with malonate (5 mol % Pd$_2$(dba)$_3$ CHCl$_3$, 25 mol % PPh$_3$, THF, rt, 2 h) afforded a mixture of 31b and 31c in a ratio of 58:42.

catalyst to 20 mol %, however, gave a much better yield (81%) with good regio-(88:12) and excellent enantioselectivity (99% ee). With a phosphate leaving group, the alkylation product was obtained in good yield (82%) and enantioselectivity (96% ee) with less catalyst (10 mol %), although the regioselectivity was much lower (entry 4).

For entry 3, 10 mol % DMSO was added to the preformed catalyst (60° C., 1 h) before the substrate and malonate were added.

TABLE 9

Alkylation of non-aromatic alkyne substrates:

32 R = CO$_2$Me
33 R = PO(OEt)$_2$

TABLE 9-continued

Alkylation of non-aromatic alkyne substrates:

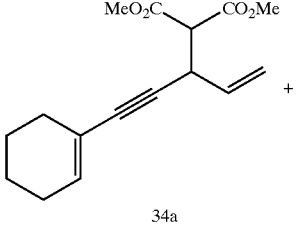

| entry | sub-strate | catalyst [mol %] | additive | time [h] | yield, % (34a + 34b) | ratio (34a:34b) | ee [%] |
|---|---|---|---|---|---|---|---|
| 1 | 32 | 10 | — | 3.5 | 36 | 79:21[e)] | 97 |
| 2 | 32 | 20 | — | 4 | 81(97) | 88:12 | 99 |
| 3 | 32 | 10 | DMSO | 3.5 | 37% conversion | 77.23[g)] | ND |
| 4 | 33 | 10 | — | 2 | 82(95) | 66:34 | 96 |

It was also observed that formation of the minor linear product in the present reactions was stereoselective. The linear product was always obtained with very high trans selectivity, generally only traces of the cis isomer were detected. This stereoselectivity was observed not only for linear carbonates but for the branched substrates as well.

As described below under the discussion of leaving groups (Section D), the present reaction can also be successfully carried out on substituents having simple alkyl substitution at the allyl terminus (e.g. crotyl chloride).

C3. Halogenated Substrates

The bromo-substituted aryl carbonate 35 was converted in 83% yield with good regio-(95:5) and enantioselectivitiy (90% ee) (Table 10). All reactions were performed in the presence of 0.1 eq Mo(CO)$_3$(EtCN)$_3$, 0.15 eq ligand, 1.0 eq substrate, 2.2 eq dimethylmalonate and 2.0 eq NaH.

TABLE 10

Asymmetric Mo-catalyzed alkylation of the carbonate 35.

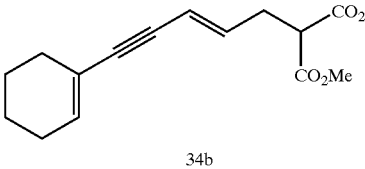

TABLE 10-continued

Asymmetric Mo-catalyzed alkylation of the carbonate 35.

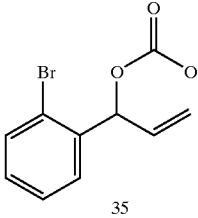

| entry | ligand | solvent | temp. [° C.] | time [h] | yield (36a + 36b) | Ratio (36a:36b) | ee [%] |
|---|---|---|---|---|---|---|---|
| 1 | (±)-I | THF | 70 | 4 | 63(94) | 94:6 | — |
| 2 | (S,S)-I | toluene/THF | 90 | 3 | 96 | 96:4 | 91 |
| 3 | III | toluene/THF | 90 | 14 | 85 | 91:9 | 88 |
| 4 | II | toluene/THF | 90 | 5 | 83(95) | 95:5 | 90 |

As can be seen from Table 10, similar enantioselectivities were achieved with all ligands employed, although the regioselectivity was somewhat lower in the case of the pyrrolidine ligand III (entry 2–4). Use of toluene/THF as solvent gave higher turnover and better regioselectivity for ligand I (entries 1–2).

The use of dialkyl phosphate leaving groups, described further below, allows the reaction to be extended to simple aliphatic substrates, e.g. crotyl diusopropyl phosphate. This reaction (carried out substantially as described above) gave reasonable regioselectivity (about 5:1 branched/linear) and good enantioselectivity (about 93%).

It should be appreciated that, although the structures of the present examples illustrate the utility and selectivity of the reaction, the allylic substrate may also form part of a more complex molecule, as in the synthesis of pharmaceutically useful chiral compounds.

D. Leaving Group

Preferred leaving groups are those which are displacable by a nucleophilic species under the conditions of the reaction, but which do not tend to dissociate without the participation of the nucleophile. These include, for example, the above described leaving groups (lower alkyl esters or carbonates) or chloride. Table 11 shows the effect on the reaction of variation of the leaving group. All reactions were performed in the presence of 0.1 eq. Mo(CO)$_3$(EtCN)$_3$, 0.15 eq. ligand, 1.0 eq. substrate, 2.2 eq. dimeth lmalonate and 2.0 eq. NaH.

TABLE 11

Variation of the leaving group

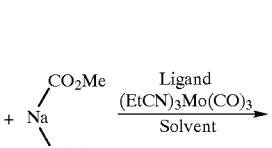

37 R = OMe
38 R = NMe$_2$
39 R = CF$_3$

TABLE 11-continued

Variation of the leaving group

| entry | substrate | solvent | temp. [° C.] | time [h] | yield (a + b) | ratio (a:b) | ee [%] |
|---|---|---|---|---|---|---|---|
| 1 | 37 | THF | 70 | 3 | 88 | 97:3 | 99 |
| 2 | 37 | THF/toluene | 90 | 2 | 96 | 96:4 | 99 |
| 3 | 38 | THF/toluene | 90 | 12 | 75(91) | 93:7 | 99 |
| 4 | 39 | THF/toluene | 90 | 4 | 94 | 93:7 | 99 |

It has been shown that carbamate and trifluoroacetate are generally useful leaving groups for Mo-catalyzed alkylation reactions (Dvorak et al., 1995). As can be seen from Table II, these groups, particulary trifluoroacetate, are also useful in the present reaction.

Variation of the leaving group was also investigated with the much less reactive crotyl substrate, using catalyst prepared from 10 mol % $Mo(CO)_3(EtCN)_3$ and 15 mol % ligand I (with the exception of entry 6, which used 20 and 30 mol %, respectively). The results are shown in Table 12.

TABLE 12

Alkyl Substrate/Phosphate Leaving Groups

| Entry | Substrate X = | Solvent | Temp | Time | Yield, % | A/B/C | e.e. of A, % |
|---|---|---|---|---|---|---|---|
| 1 | Cl | THF | 60° C. | 2h | 76 | 2.1/1 (A/B + C) | 82 |
| 2 | Cl | THF | RT | 2h | 65 | 1.9/1 (A/B + C) | 75 |
| 3 | Cl | THF/toluene | 60° C. | 5h | 79 | 2.6/1 (A/B + C) | 79 |
| 4 | O(P=O)Ph$_2$ | THF | 65° C. | 4h | 70 | 2.5/1/0.13 | 85 |
| 5 | O(P=O)(OEt)$_2$ | THF | 65° C. | 1h | 82 | 4.4/1/0.17 | 89 |
| 6 | O(P=O)(OEt)$_2$ | THF | 65° C. | 1h | 71 | 5.1/1/0.26 | 89 |
| 7 | O(P=O)(OPh)$_2$ | THF | 65° C. | 1h | — | — | — |
| 8 | O(P=O)(OiPr)$_2$ | THF | 65° C. | 1h | 72 | 5.7/1/0.19 | 93 |

Product C is generated by the competing uncatalyzed displacement reaction. Changing the leaving group from chloride to diphenyl phosphinate gave similar results, and the diphenyl phosphate substrate gave no reaction. Reaction of the diethyl phosphate, however, gave alkylated product with higher regioselectivity as well as good enantioselectivity. Use of a large amount of catalyst (20 mol %), or a bulkier leaving group, dilsopropyl phosphate (last entry), reduced competition from the uncatalyzed $S_N2$ reaction and gave still better results.

These results represent the most successful demonstration to date, in terms of regioselectivity and enantioselectivy, of allylic alkylation of an aliphatic allyl group. It should be noted that the reduction in regioselectivity in these reactions is believed to be primarily (if not exclusively) due to the competing uncatalalyzed reaction, which is nonselective. The catalyzed reaction is still highly stereoselective, as shown by the high e.e. of the addition products A. Reaction of substrates having bulkier substituents, and/or having the leaving group at the secondary position of the allyl group (i.e. the 1 terminus), is expected to give improved results.

E. Nucleophile (Alkylating Agent)

An ongoing challenge in molybdenum catalyzed allylic alkylations has been the limited range of effective nucleophiles. Historically, only malonates have given consistent results. In the present reaction, however, other nucleophiles have proven effective. Preferred nucleophiles may be represented as $EE^-RC^-M^+$, where $M^+$ is a positively charged counterion, and each of E and E' is a substituent which stabilizes the carbanion, e.g. an electron-withdrawing substituent selected from keto, carboxylic ester, cyano, and sulfonyl, or an aromatic or heteroaromatic group capable of stabilizing an α-carbanion. Preferably, at least one of E and E' is a carboxylic ester. Particularly preferred are malonates, including substituted malonates, as described below, acyclic β-ketoesters, and β-cyano esters. Nucleophiles in which E is a carboxylic ester and E' is an aromatic group, such as phenyl or pyridyl, have also proven effective. In general, a wider range of nucleophiles will be effective when the substrate has an active leaving group, such as a dialkyl phosphate. Table 13 shows the results of alkylations using a β-keto ester, methyl acetoacetate.

TABLE 13

Alkylations with methyl acetoacetate (acac)

| Substrate; X = | Mo mol % | Ligand mol % | Solvent | Temp | Time | Yield, % | A/B | ee of C, % |
|---|---|---|---|---|---|---|---|---|
| (a); OCO₂Me | 20 | 30 | THF | 65° C. | 18 h | 25 | >40/1 | — |
| (b); OCO₂Me | 10 | 15 | THF | 65° C. | 22 h | 47(61) | >50/1 | 84 |
| (b); OCO₂Me | 20 | 30 | THF | 65° C. | 8 h | 66(72) | 53/1 | 92 |
| (b); OCO₂Me | 10 | 15 | THF/toluene | 90° C. | 18 h | 54(68) | 15/1 | — |
| (a); O(P=O)(OEt)₂ | 10 | 15 | THF | 65° C. | 20 h | 72 | 9.7/1 | 97 |
| (a); O(P=O)(OEt)₂ | 20 | 30 | THF | 65° C. | 4 h | 85 | 46/1 | 98 |

Substrates having a phosphate leaving group (e.g. cinnamyl phosphate) showed greater reactivity with this nucleophile, but also showed increased product from the uncatalyzed reaction. When increased catalyst (20 mol %) was used, the amount of competing product decreased, and regioselectivity was improved.

The β-ketoester methyl p-methoxy-benzoylacetate (below) reacted with cinnamyl phosphate to give a 1:1 diastereomeric mixture of allylic alkylation product in good regioselectivity. Enantioselectivity was determined, after decarboxylation of the compound, to be >99%.

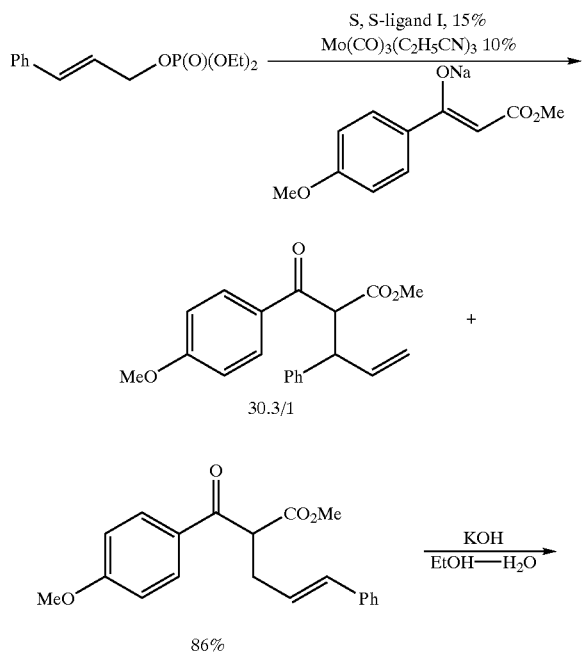

Substituted malonates can also be used in the present reaction. For example, reaction of carbonate 40 with dimethyl sodio methylmalonate gave, after hydrolysis and decarboxylation, acid 42 (most probably as a diastereoisomeric mixture at position 2), the methyl ester of which is methyl mantolinate, a monoterpene constituent of *Artemesia tridentada tridentada*.

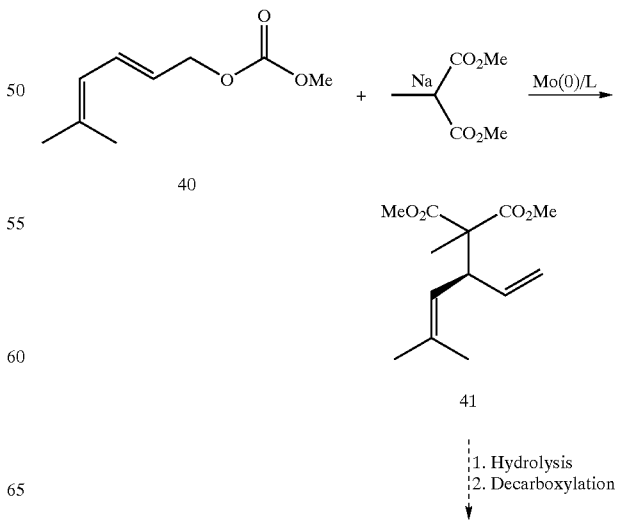

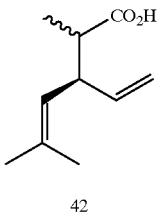

42

Good results were also obtained using malonates substituted at the nucleophilic carbon with protected alcohol or amine moieties (methoxymethyl ether and NH-Boc, respectively), and with β-cyano esters (e.g. t-butyl cyano acetate). Increasing the amount of catalyst to 20 mol % metal/30 mol % ligand was sometimes required. The reactions gave good regioselectivity and excellent enantioselectivity (generally >98%).

IV. Intramolecular Diels-Alder Reactions

Figure 5:
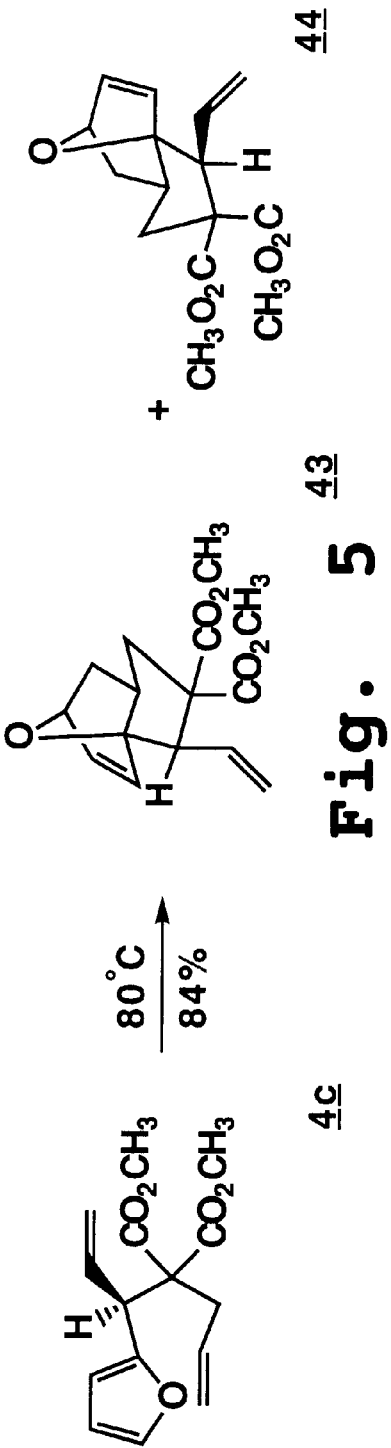
FIG. 5 illustrates the intramolecular Diels-Alder reaction of the product of reaction 14, Table 1, which was prepared according to the method of the invention.

The usefulness of the present stereo- and regioselective alkylation reaction was further demonstrated by subsequent Diels-Alder reaction, shown in FIG. 5, of the alkylation product of reaction 14, Table 1, predominantly 4c (R=allyl). Heating the product at 80° C. in 5:2 water:ethanol gave the diastereomeric Diels-Alder adducts 43 and 44 (FIG. 5) in a 3:1 ratio, each of which had an e.e. of 98%. as determined by chiral HPLC.

In another example, Mo-catalyzed reaction of methyl cinnamyl carbonate with dimethyl (2E,4E)-hexadienyl malonate afforded the branched product 45 in 60% yield with very good enantioselectivity (>94% ee) (see below). Heating the alkylation product 45 at 150° C. in toluene (sealed tube) for 48 hours gave a 73% yield of a product tentatively identified as the Diels-Alder adducts 46, as a mixture of three isomers in a 49:44:7 ratio, as determined by integration of the $^1$H NMR methoxycarbonyl signals. (Apparently one of the four theoretically possible Diels-Alder adducts was not formed.)

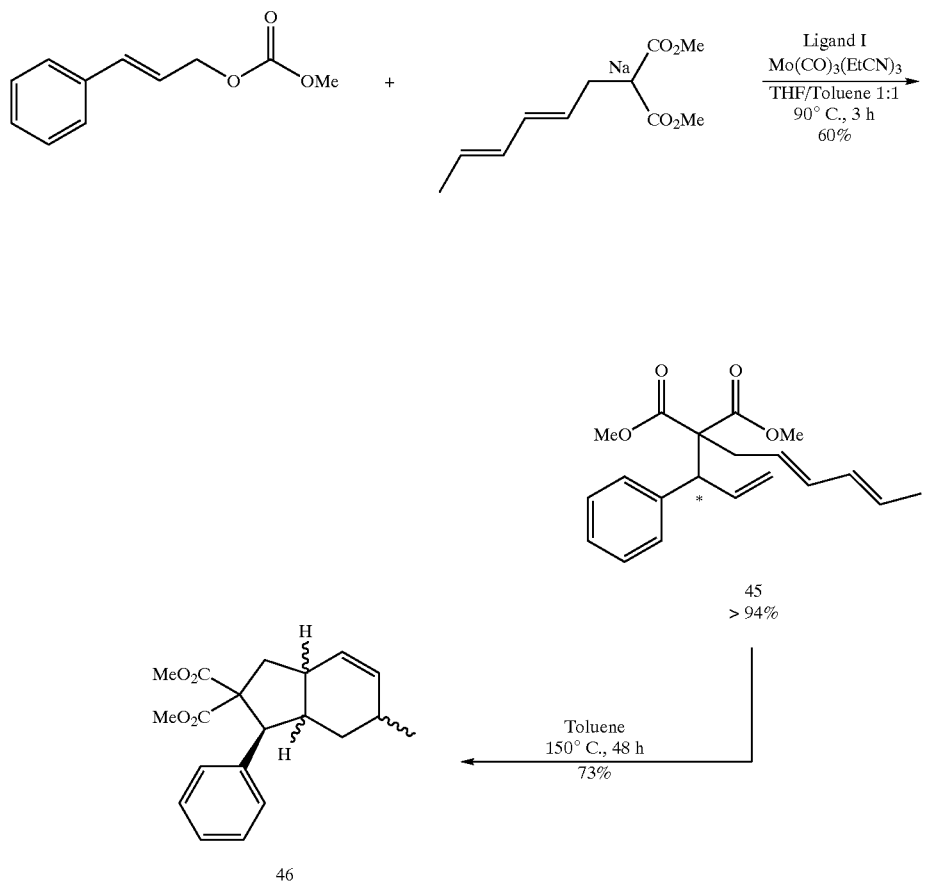

As a further example, when substrate 26, below, was reacted with dimethyl allylmalonate, a 5:1 mixture of two compounds was obtained (below). The branched isomer 47 was isolated in pure form in 71% yield. Heating 47 at 150° C. in toluene (sealed tube) for 15 hours afforded a product tentatively identified as the Diels-Alder adducts 48, as a mixture of four isomers in a 3:3:1:1 ratio, as determined by integration of the $^1$H NMR methoxycarbonyl signals.

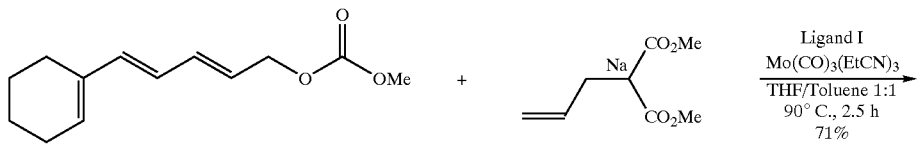

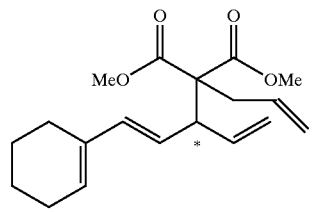

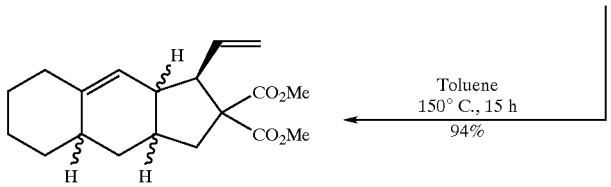

V. Advantages

The present reaction displays high selectivity over a wide temperature range, suggesting a fairly rigid chiral active site. The regioselectivity observed for attack at the more substituted terminus is generally significantly higher than with earlier achiral molybdenum catalysts. For example, as noted previously, previous molybdenum-catalyzed alkylations with dimethyl methylmalonate and cinnamyl substrates (Trost & Lautens, 1982, 1987, Trost & Merlic, 1990) normally led to attack at the less substituted allyl terminus. With the chiral ligands described herein, on the other hand, good selectivity for attack at the more substituted terminus is seen for a wide range of substrates.

The rate of reaction is also significantly improved compared to earlier molybdenum catalysts, where reaction typically required heating at reflux for 24 h or more (Trost & Lautens, 1982, 1987, Trost & Merlic, 1990, Merlic, 1988). Chiral ligands employed in Merlic (1988) also gave low e.e.'s in the product. In contrast, the reactions reported herein typically proceed in 2–3 h at reflux and less than 24 h at room temperature, and give high enantioselectivity.

The reaction also shows great versatility in terms of substrate, as shown above, giving good results with polyenes, halogenated substrates, various aryl substrates, and unprecedented success with non-aromatic substrates. The selectivity and versatility of the reaction make the method ideal for the synthesis of pharmaceutical compounds, or compounds employed as intermediates in the synthesis of pharmaceutical compounds. The method is also applicable to preparing other biologically active compounds where chirality is important to activity.

EXAMPLES

The following examples are intended to illustrate but not in any way limit the invention.

Materials and Methods

All reactions were carried out in flame-dried flasks or test tubes under a positive pressure of nitrogen. Solvents were generally distilled prior to use and transferred via syringe to the reaction vessel. $^1$H NMR and $^{13}$C NMR spectra were recorded on Varian Gemini-200 or 300. Optical Rotations were determined using a JASCO DIP-1000 polarimeter and were measured in 50 mm cells at 25±2° C. Infrared (IR) spectra [cm$^{-1}$] were obtained using a Perkin-Elmer FT-IR spectrometer. Melting points (mp) were determined in open capillary tubes using a Thomas-Hoover apparatus and are un-corrected. Thin-layer chromatography (TLC) was performed on precoated glass plates (Merck). Flash chromatography was performed by the method of Still (Still, et al., 1978) using silica gel 60, 230–400 mesh. The enantiomeric excess was determined by analytical, enantioselective HPLC using the following columns with chiral stationary phases: Daicel Chiralcel® OD, Daicel Chiralpak® AD, and Daicel Chiralcel® OJ. Unless otherwise indicated, reported e.e. refers to major isomer. Solvent systems, flow rates (in mLmin$^{-1}$) and retention times (in min) are as indicated; UV-detection (220 nm). High-resolution Mass spectra were provided by the Mass Spectronomy Facility of the School of Pharmacy (University of California, San Francisco), and combustion analyses were performed by M-H-W Laboratories, Phoenix, Ari.

Substrates were synthesized according to published procedures or using standard synthetic methods well known in the art. Reactions frequently employed were addition of vinylmagnesium bromide to aldehydes (e.g. Hammen et al., 1991), the Wadsworth-Homer-Emmons reaction of aldehydes with triethylphosphonoacetate, and DIBAL-H reduction of unsaturated ethyl esters. The method of Hung, 1984, was used for the preparation of allylic carbonates.

All alkylation reactions were performed in degassed (with nitrogen or argon) solvents. Ratios of regioisomers (determined by $^1$H NMR) and enantiomeric excess were determined from the isolated products. Absolute stereochemistry was assigned only in the cases where direct comparison of the optical rotation with literature values was possible. The $^1$H NMR data of the minor isomer were normally assigned with the assistance of a $^1$H NMR spectrum independently obtained by a palladium(0)-catalyzed reaction. In the palladium reactions the linear trans-isomer was always the major product, although with many substrates significant amounts of its cis-isomer and/or of the branched product were also formned.

Example 1

General Prodedure A; THF as Solvent (see Trost and Hachiya, 1998).

A solution of Mo(CO)$_3$(EtCN)$_3$ and ligand in THF was heated at 60–70° C. for 1 h. A solution of sodiomalonate (prepared by adding the malonate to sodium hydride (60% dispersion in oil; purchased from Aldrich)) and the substrate in THF was added dropwise via syringe at 60° C. and the mixture was heated at 70° C. for the time indicated. The reaction mixture was diluted with ether (5 mL) and water (5 mL) was added. The layers were separated and the aqueous layer was extracted with ether (3×10 mL). The combined organic layers were washed with brine (10 mL), dried over magnesium sulfate and the solvent removed in vacuo. Flash chromatography (with the solvent system indicated) afforded the pure product as a mixture of the two regioisomers.

Example 2

General Procedure B; Toluene/THF 1:1 as Solvent

A solution of Mo(CO)$_3$(EtCN)$_3$ and ligand in toluene was heated at 60–70° C. for 1 h. A solution of sodiomalonate (prepared by adding the malonate to sodium hydride (60% dispersion in oil)) and the substrate in THF was added dropwise via syringe at 60° C. and the mixture was heated at 80–90° C. for the time indicated. The reaction mixture was diluted with ether (5 mL) and water (5 mL) was added. The layers were separated and the aqueous layer was extracted with ether (3×10 mL). The combined organic layers were washed with brine (10 mL), dried over magnesium sulfate and the solvent removed in vacuo. Flash chromatography (with the solvent system indicated) afforded the product as a mixture of the two regioisomers.

Examples 3A–3D

Preparation of (S)-Methyl 2-methoxycarbonyl-3-phenyl-4-pentenoate and Methyl (E)-2-Methoxycarbonyl-5-phenyl-4-pentenoate (Lloyd-Jones and Pfalz, 1995; Trost and Hachiya, 1998; Hung, 1984)

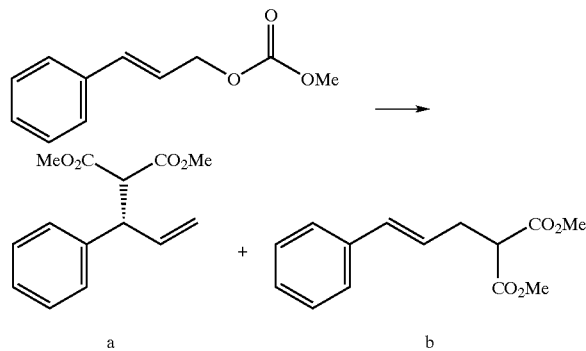

a            b

A. Mo-catalyzed Alkylation with Pyrrolidine Ligand III:

According to procedure A with Mo(CO)$_3$(EtCN)$_3$ (13.0 mg, 0.038 mmol) and ligand III (21.9 mg, 0.056 mmol) in 1.5 mL THF and carbonate (72.4 mg, 0.34 mmol), dimethyl malonate (109.4 mg, 0.83 mmol) and sodium hydride (30.0 mg, 0.75 mmol) in 1.5 mL THF. The reaction mixture was heated at 70° C. for 18 h. Work-up and flash chromatography (petroleum ether/ether 6:1) afforded 20 mg recovered starting material and 37 mg (40%; 55% brsm) of a colorless oil consisting of a mixture of regioisomers; a/b 82:18. [α]D== 27.1 (c 1.43, CHCl$_3$). 94% ee.

B. According to procedure B with Mo(CO)$_3$(EtCN)$_3$ (9.0 mg, 0.026 mmol) and ligand III (15.7 mg, 0.039 mmol) in 1.3 mL toluene and carbonate (50.1 mg, 0.26 mmol), dimethyl malonate (75.8 mg, 0.57 mmol) and sodium hydride (20.9 mg, 0.52 mmol) in 1.3 mL THF. The reaction mixture was heated at 90° C. for 8 h. Work-up and flash chromatography (petroleum ether/ether 6:1) afforded 15 mg recovered starting material and 49.0 mg (76%; 98% brsm) of a colorless oil consisting of a mixture of regioisomers; a/b 89:11. [α]$_D$=−25.0 (c 1.53, CHCl$_3$). 94% ee.

C. Mo-catalyzed Alkylation with Diphenyl Ligand II:

According to procedure A with Mo(CO)$_3$(EtCN)$_3$ (8.3 mg, 0.024 mmol) and ligand II (15.2 mg, 0.036 mmol) in 1.5 mL THF and carbonate (46.0 mg, 0.24 mmol), dimethyl malonate (69.0 mg, 0.53 mmol) and sodium hydride (19.0 mg, 0.22 mmol) in 1 mL THF. The reaction mixture was heated at 70° C. for 8 h. Work-up and flash chromatography (petroleum ether/ethyl acetate 20:1) afforded 8.0 mg recovered starting material and 43.9 mg (74%; 89% brsm) of a colorless oil consisting of a mixture of regioisomers; a/b 92:8. [α]$_D$=−32.9 (c 2.00, CHCl$_3$). 98% ee.

D. According to procedure B with Mo(CO)$_3$(EtCN)$_3$ (7.8 mg, 0.023 mmol) and ligand II (14.3 mg, 0.034 mmol) in 1.5 mL toluene and carbonate (43.8 mg, 0.23 mmol), dimethyl malonate (66.4 mg, 0.50 mmol) and sodium hydride (18.3 mg, 0.46 mmol) in 1 mL THF. The reaction mixture was heated at 90° C. for 3 h. Work-up and flash chromatography (petroleum ether/ethyl acetate 20:1) afforded 53.8 mg (95%) of a colorless oil consisting of a mixture of regioisomers; a/b 95:5. [α]$_D$=−34.5 (c 1.92, CHCl$_3$). 99% ee.

Example 4

Preparation of Dimethyl 2-(1-Phenyl-allyl)-malonate Using Ligand IV

Cycloheptyl ligand IV (10.2 mg, 0.030 mmol) and Mo(CO)$_3$(EtCN)$_3$ (6.9 mg, 0.020 mmol) were dissolved in 1.0 ml of THF at rt. The reaction mixture was heated at 60° C. for 1 h. After cooling to rt, 1.0 ml of THF solution of sodium dimethylmalonate enolate, prepared from dimethyl malonate (58.0 mg, 0.44 mmol) and sodium hydride (10.2 mg, 0.40 mmol) in tetrahydrofuran, and methyl 3-phenyl-2-propenyl carbonate were added successively. The reaction mixture was heated at 65° C. for 8 h. The reaction mixture was poured into water and extracted with ethyl acetate. The combined organic layers were dried over sodium sulfate, and the solvent was removed under reduced pressure. The ratio of 1,1-dimethoxycarbonyl-2-phenyl-3-butene and linear compound was determined by $^1$H NMR (400 MHz) to be 34.2/1. The residue was chromatographed on silica (1/8 ethyl acetate/petroleum ether, Rf=0.3) to yield the mixture of branched and linear compound (36.7 mg, 74%). [α]$_D$−29.7° (c 1.27, CHCl$_3$); 99% ee.

Examples 5A–B

Preparation of Dimethyl 2-(1-thiolphene-2-yl-allyl)-malonate Using Ligands IV and VIII Cycloheptyl ligand IV (10.2 mg, 0.030 mmol) and Mo(CO)$_3$(EtCN)$_3$ (6.9 mg, 0.020 mmol) were dissolved in 1.0 ml of THF at rt. The reaction mixture was heated at 60° C. for 1 h. After cooling to rt., 1.0 ml of THF solution of sodium dimethylmalonate enolate, prepared from dimethyl malonate (58.0 mg, 0.44 mmol) and sodium hydride (10.2 mg, 0.40 mmol) in tetrahydrofuran, and methyl 1-(2-thienyl)-2-propenyl carbonate were added successively. The reaction mixture was heated at 65° C. for 4.5 h. The reaction mixture was poured into water and extracted with ethyl acetate. The combined organic layers were dried over sodium sulfate, and the solvent was removed under reduced pressure. The ratio of dimethyl 2-(1-thiophene-2-yl-allyl)-malonate and linear compound was determined by $^1$H NMR (400 MHz) to be 16.0/1. The residue was chromatographed on silica (1/7 ethyl acetate/petroleum ether, Rf=0.3) to yield the mixture of branched and linear compound. (40.3 mg, 78%) $[\alpha]_D$–31.1° (c 1.35, CHCl$_1$); 92% e.e. for major isomer.

When the reaction was repeated using ligand VIII, the regioisomer ratio of the product, obtained in 83% yield, was determined to be 12.7/1. $[\alpha]_D$=+30.2°; 84% e.e. for major isomer.

Example 6

Preparation of Methyl (4E)-2-Methoxycarbonyl-5-phenyl-3-vinyl-4-pentenoate 12a and Methyl (4E, 6E)-2-methoxycarbonyl-7-phenyl-4,6-heptadienoate 12b

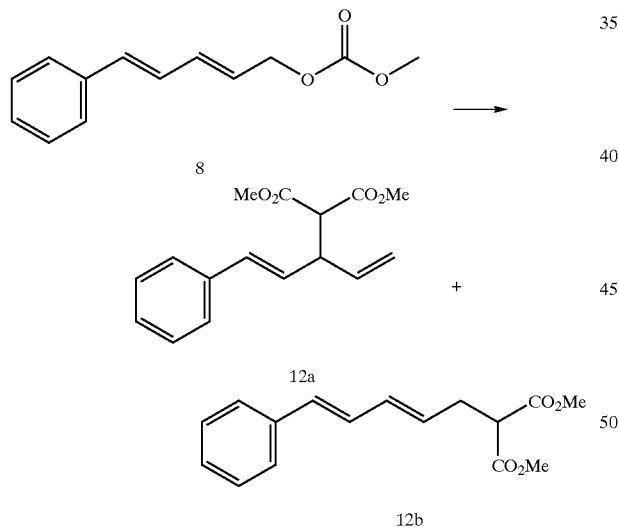

According to procedure B with Mo(CO)$_3$(EtCN)$_3$ (6.4 mg, 0.0188 mmol) and ligand IV (11.7 mg, 0.0282 mmol) in 1 mL toluene and carbonate 8 (40.5 mg, 0.185 mmol), dimethyl malonate (53.9 mg, 0.41 mmol) and sodium hydride (14.8 mg, 0.37 mmol) in 1 mL THF. The reaction mixture was heated at 90° C. for 3 h. Work-up and flash chromatography (petroleum ether/ether 10:1) afforded 48.5 mg (95%) of 12 as a colorless oil consisting of a mixture of regioisomers; 12a/12b 86:14. $[\alpha]_D$=–15.7 (c 2.51, CHCl$_3$). 98% ee, major isomer.

Examples 7A–7B

Preparation of Methyl (4E,6E)-2-Methoxycarbonyl-7-phenyl-3-vinyl-4,6-heptadienoate 13a and Methyl (4E,6E,8E)-2-Methoxycarbonyl-9-phenyl-4,6,8-nonatrienoate 13b

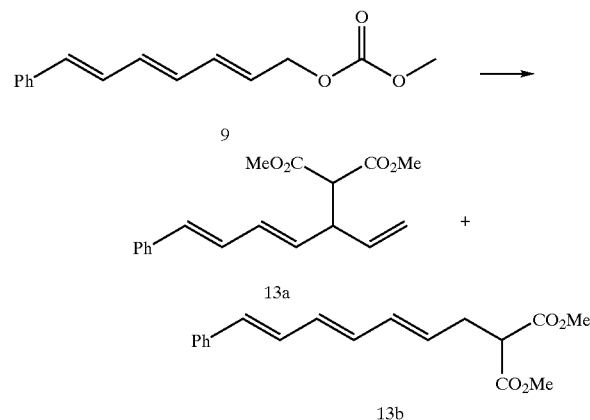

A. According to procedure B with Mo(CO)$_3$(EtCN)$_3$ (3.1 mg, 0.009 mmol) and ligand II (5.7 mg, 0.014 mmol) in 0.7 mL toluene and carbonate 9 (21.9 mg, 0.090 mmol), dimethyl malonate (26.1 mg, 0.198 mmol) and sodium hydride (7.2 mg, 0.180 mmol) in 0.7 mL THF. The reaction mixture was heated at 90° C. for 4 h. Work-up and flash chromatography (petroleum ether/ether 6:1) afforded 8.1 mg of starting material and 15.6 mg (58%; 92% brsm) of 13 as a colorless oil consisting of a mixture of regio-isomers; 13a/13b 84:16. $[\alpha]_D$=–42.1 (c 0.51, CH$_2$Cl$_2$). 97% ee.

B. According to procedure B with Mo(CO)$_3$(EtCN)$_3$ (5.4 mg, 0.016 mmol) and ligand (R,R)-I (7.6 mg, 0.024 mmol) in 1 mL toluene and carbonate 9 (25.5 mg, 0.104 mmol), dimethyl malonate (30.2 mg, 0.23 mmol) and sodium hydride (8.4 mg, 0.21 mmol) in 1 mL THF. The reaction mixture was heated at 85° C. for 3.5 h. Work-up and flash chromatography (petroleum ether/ether 6:1) afforded 11.8 mg of starting material and 21.4 mg (68%; 94% brsm) of 13 as a colorless oil consisting of a mixture of regio-isomers; 13a/13b 86:14. $[\alpha]_D$=–44.9 (c 0.40, CH$_2$Cl$_2$). >99% ee.

Example 8

Preparation of Methyl (4E)-2-Methoxycarbonyl-4-methyl-3-vinyl-4-hexenoate 21a and Methyl (4E, 6E)-2-Methoxycarbonyl-6-methyl-4,6-octadienoate 21b

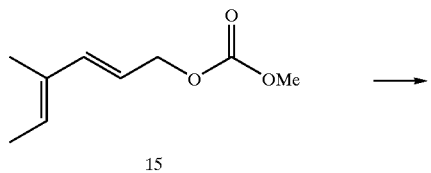

-continued

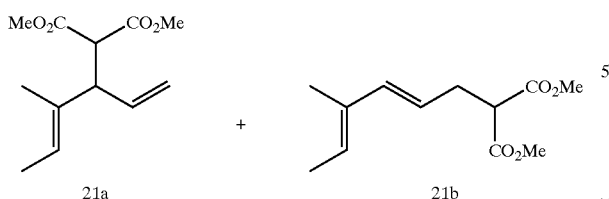

21a

21b

According to procedure B with Mo(CO)$_3$(E$^{tc}$N)$_3$ (7.5 mg, 0.0$_2$2 mmol) and ligand (R,R)-I (10.7 mg, 0.035 mmol) in 1 mL toluene and carbonate 15 (37.0 mg, 0.217 mmol), dimethyl malonate (63.2 mg, 0.48 mmol) and sodium hydride (17.4 mg, 0.44 mmol) in 1 mL THF. The reaction mixture was heated at 90° C. for 3 h. Work-up and flash chromatography (petroleum ether/ether 8:1) afforded 43.8 mg (89%; 94% brsm) of 21 as a colorless oil consisting of a mixture of regioisomers; 21a/21b 98:2. [α]$_D$=+10.3 (c 0.06, CH$_2$Cl$_2$). 98% ee.

Example 9

Preparation of Methyl 3-(1-Cyclopenten-1-yl)-2-methoxycarbonyl-4-pentenoate 23a and Methyl (E)-5-(1-Cyclopenten-1-yl)-2-methoxycarbonyl-4-pentenoate 23b

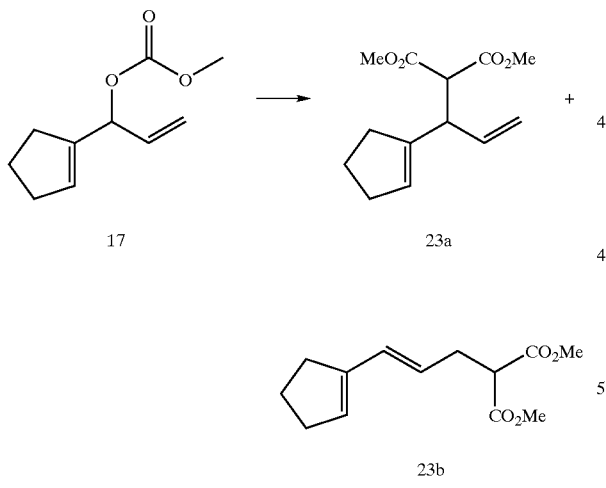

17

23a

23b

According to procedure B with Mo(CO)$_3$(EtCN)$_3$ (10.5 mg, 0.030 mmol) and ligand (R,R)-I (14.8 mg, 0.046 mmol) in 1.5 mL toluene and carbonate 17 (58.4 mg, 0.32 mmol), dimethyl malonate (88.4 mg, 0.67 mmol) and sodium hydride (24.3 mg, 0.61 mmol) in 1.5 mL THF. The reaction mixture was heated at 90° C. for 2 h. Work-up and flash chromatography (petroleum ether/ether 10:1) afforded 72.0 mg (94%) of 23 as a colorless oil consisting of a mixture of regioisomers; 23a/23b 92:8. [α]$_D$=−52.1 (c 3.15, CH$_2$Cl$_2$). 87% ee.

Example 10

Preparation of Methyl 3-(2-Dihydropyranyl)-2-methoxycarbonyl-4-pentenoate 25a and Methyl (5E)-6-(2-Dihydroipyranyl)-2-methoxycarbonyl-5-hexenoate 25b

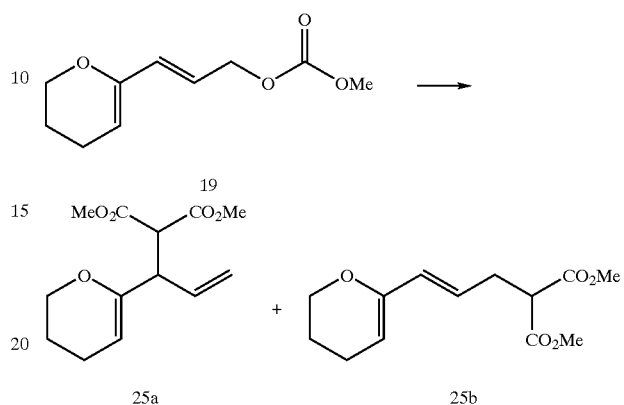

19

25a

25b

According to procedure B with Mo(CO)$_3$(EtCN)$_3$ (12.5 mg, 0.036 mmol) and ligand (R,R)-I (17.6 mg, 0.054 mmol) in 1.8 mL toluene and carbonate 19 (35.9 mg, 0.18 mmol), dimethyl malonate (52.6 mg, 0.40 mmol) and sodium hydride (14.5 mg, 0.36 mmol) in 1.0 mL THF. The reaction mixture was heated at 90ocC for 1.5 h. Work-up and flash chromatography (petroleum ether/ether 6:1) afforded 42.8 mg (93%) of 25 as a colorless oil consisting of a mixture of regioisomers; 25a/25b 93:7. [α]$_D$=−11.9 (c 2.00, CH$_2$Cl$_2$). 96% ee.

Example 11

Methyl (4E,6E)-2-Methoxycarbonyl-3-vinyl-4,6-octadienoate 29a and Methyl (4E,6E,8E)-2-Methoxycarbonyl-4,6,8-decatrienoate 29b

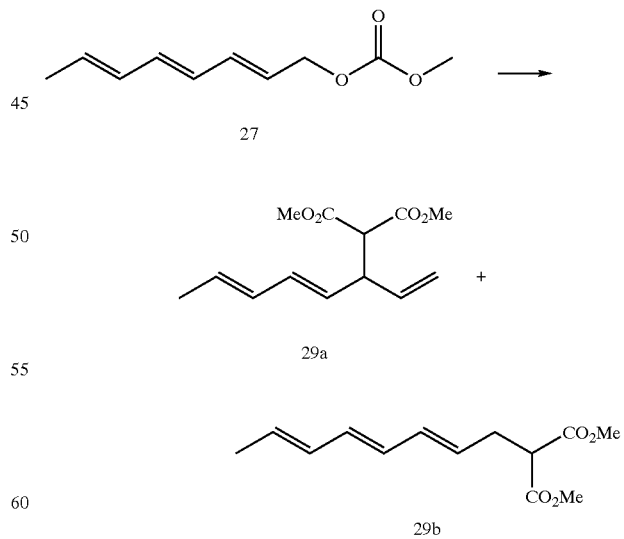

27

29a

29b

According to procedure B with Mo(CO)$_3$(EtCN)$_3$ (9.8 mg, 0.028 mmol) and ligand (R,R)-I (13.8 mg, 0.043 mmol) in 1.5 mL toluene and carbonate 27 (51.7 mg, 0.28 mmol), dimethyl malonate (82.5 mg, 0.63 mmol) and sodium

39 hydride (22.7 mg, 0.57 mmol) in 1.5 mL THF. The reaction mixture was heated at 85° C. for 3 h. Workup and flash chromatography (petroleum ether/ether 8:1) afforded besides 2.5 mg starting material 54.5 mg (81%; 85% brsm) of 29 as a colorless oil consisting of a mixture of regioisomers; 29a/29b 91:9. $[\alpha]_D$=−15.0 (c 2.00, $CH_2Cl_2$). 98% ee.

Examples 12A–B

Preparation of Methyl 2-Methoxycarbonyl-5-phenyl-3-vinyl-4-pentynoate 31a and Methyl (4E)-2-Methoxycarbonyl-7-phenyl-hept-4-en-6-ynoate 31b

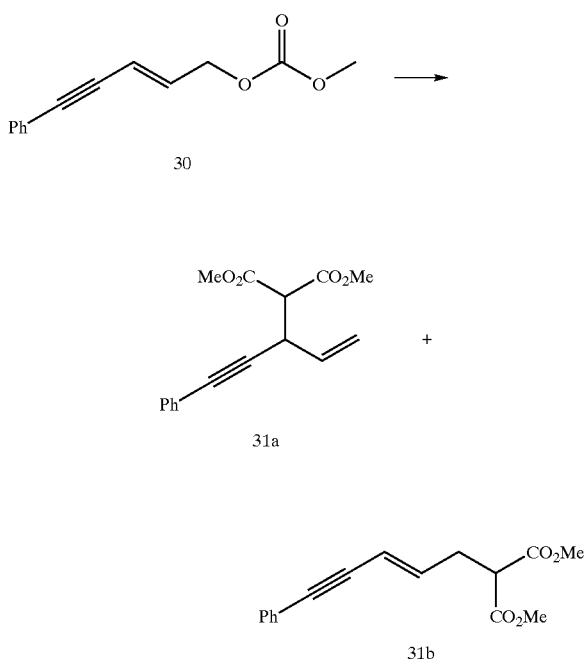

A. According to procedure B with $Mo(CO)_3(EtCN)_3$ (6.2 mg, 0.018 mmol) and ligand (R,R)-I (8.7 mg, 0.027 mmol) in 1 mL toluene and carbonate 30 (36.4 mg, 0.17 mmol), dimethyl malonate (52.2 mg, 0.40 mmol) and sodium hydride (14.4 mg, 0.36 mmol) in 1.0 mL THF. The reaction mixture was heated at 85° C. for 2.5 h. Work-up and flash chromatography (petroleum ether/ether 8:1) afforded besides 5 mg starting material 37.6 mg (82%; 95 brsm) of 31 as a colorless oil consisting of a mixture of regioisomers; 31a/31b 84:16. $[\alpha]_D$=−86.6 (c 1.40, $CH_2Cl_2$). 99% ee.

B. Pd-catalyzed reaction: To solution of $Pd_2(dba)_3$-$CHCl_3$ (9.5 mg, 0.0092 mmol) and triphenylphosphine (12.1 mg, 0.046 mmol) in 2 mL THF was added a solution of 30 (39.8 mg, 0.184 mmol) and dimethyl malonate (48.7 mg, 0.37 mmol) in 2 mL THF. After 2 h at r.t. the mixture was diluted with ether (5 mL) and water (5 mL) was added. The layers were separated and the aqueous layer was extracted with ether (3×10 mL). The combined organic layers were washed with brine (10 mL), dried over magnesium sulfate the solvent removed in vacuo. Flash chromatography (petroleum ether/ether 8:1) afforded 48.0 mg (96%) of a mixture of 31b and 31c in a ratio of 58:42.

40

Example 13

Preparation of Methyl 3-(2-Bromophenyl)-2-methoxycarbonyl-4-pentenoate 36a and Methyl (E)-5-(2-Bromophenyl)-2-methoxycarbonyl-4-pentenoate 36b

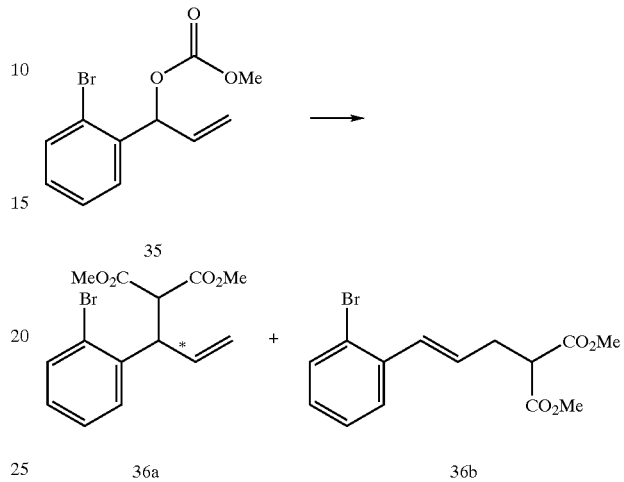

According to procedure B with $Mo(CO)_3(EtCN)_3$ (4.8 mg, 0.0139 mmol) and ligand (S,S)-I (6.8 mg, 0.021 mmol) in 0.6 mL toluene and carbonate 35 (37.7 mg, 0.14 mmol), dimethyl malonate (40.4 mg, 0.306 mmol) and sodium hydride (11.1 mg, 0.28 mmol) in 0.8 mL THF. The reaction mixture was heated at 90° C. for 3 h. Work-up and flash chromatography (petroleum ether/ethyl acetate 10:1) afforded 43.5 mg (96%) of 36 as a colorless oil consisting of a mixture of regioisomers; 36a/36b 96:4. $[\alpha]_D$=+42.5 (c 2.60, $CH_2Cl_2$). 91% ee.

Example 14

Preparation of Methyl 2-Methoxycarbonyl-3-phenyl-4-pentenoate a and Methyl (E)-2-Methoxycarbonyl-5-phenyl-4-pentenoate b Using a Variety of Leaving Groups According to procedure B with $Mo(CO)_3(EtCN)_3$ (7.5 mg, 0.022 mmol) and ligand (S,S)-I (4.2 mg, 0.013 mmol) in 1 mL toluene and carbonate 37 (41.8 mg, 0.22 mmol), dimethyl malonate (62.9 mg, 0.48 mmol) and sodium hydride (17.3 mg, 0.44 mmol) in 1 mL THF. The reaction mixture was heated at 80° C. for 2 h. Work-up and flash chromatography (petroleum ether/ether 6:1) afforded 51.8 mg (96%) of a colorless oil consisting of a mixture of regioisomers; a/b 96:4. 99% ee.

According to procedure B with $Mo(CO)_3(EtCN)_3$ (7.6 mg, 0.022 mmol) and ligand (S,S)-I (10.7 mg, 0.039 mmol) in 1.0 mL toluene and carbamate 38 (45.0 mg, 0.22 mmol), dimethyl malonate (63.4 mg, 0.48 mmol) and sodium hydride (17.6 mg, 0.44 mmol) in 1 mL THF. The reaction mixture was heated at 90° C. for 24 h. Work-up and flash chromatography (petroleum ether/ether 6:1) afforded 41.0 mg (75%; 91% brsm) of a colorless oil consisting of a mixture of regioisomers; a/b 93:7. 99% ee.

According to procedure B with $Mo(CO)_3(EtCN)_3$ (3.0 mg, 0.0087 mmol) and ligand (S,S)-I (4.2 mg, 0.013 mmol) in 0.5 mL toluene and trifluoroacetate 39 (20.0 mg, 0.087 mmol), dimethyl malonate (25.1 mg, 0.19 mmol) and sodium hydride (7.0 mg, 0.17 mmol) in 0.8 mL THF. The reaction mixture was heated at 80° C. for 4 h. Work-up and flash chromatography (petroleum ether/ether 6:1) afforded 20.2 mg (94%) of a colorless oil consisting of a mixture of regioisomers; a/b 93:7.99% ee.

Examples 15A–B

Preparation of Methyl 2-Methoxycarbonyl-5-(1-cyclohexen-1-yl)-3-vinyl-4-pentynoate 34a and Methyl (4E)-2-Methoxycarbonyl-7-(1-cyclohexen-1-yl)-hept-4-en-6-ynoate 34b Using Different Leaving Groups A. According to procedure B with Mo(CO)$_3$(EtCN)$_3$ (8.1 mg, 0.024 mmol) and ligand (R,R)-I (11.4 mg, 0.035 mmol) in 1.2 mL toluene and carbonate 32 (25.8 mg, 0.12 mmol), dimethyl malonate (34.1 mg, 0.26 mmol) and sodium hydride (9.4 mg, 0.24 mmol) in 1.0 mL THF. The reaction mixture was heated at 85° C. for 4.5 h. Work-up and flash chromatography (petroleum ether/ether 8:1) afforded besides 4.2 mg starting material 26.2 mg (81%; 97% brsm) of 34 as a colorless oil consisting of a mixture of regioisomers; 34a/34b 88:12. [α]$_D$=−63.9 (c 1.25, CH$_2$Cl$_2$). 99% ee.

B. According to procedure B with Mo(CO)$_3$(EtCN)$_3$ (7.5 mg, 0.022 mmol) and ligand (R,R)-I (10.6 mg, 0.033 mmol) in 1 mL toluene and phosphate 33 (64.8 mg, 0.22 mmol), dimethyl malonate (63.2 mg, 0.48 mmol) and sodium hydride (17.4 mg, 0.44 mmol) in 1.0 mL THF. The reaction mixture was heated at 90° C. for 2 h. Work-up and flash chromatography (petroleum ether/ether 5:1) afforded 49.8 mg (82%; 95% brsm) of 34 as a colorless oil consisting of a mixture of regioisomers; 34a/34b 66:34. 96% ee.

Example 16

Reaction of Methyl 3-(3-Phenylpropenyl) Carbonate with Sodio Methyl Acetoacetate

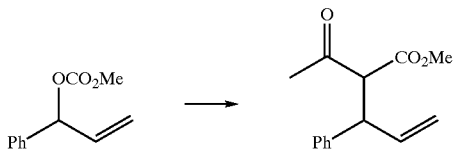

S, S-ligand I (19.4 mg, 0.060 mmol) and Mo(CO)$_3$(EtCN)$_3$ (13.8 mg, 0.04 mmol) were dissolved in 1.0 ml of tetrahydrofuran at rt, and the reaction mixture was heated at 60° C. for 1 h. After cooling to rt., a solution of sodio methyl acetoacetate in 1.0 ml of tetrahydrofuran, prepared from methyl acetoacetate (51.1 mg, 0.44 mmol) and sodium hydride (10.2 mg, 0.40 mmol) in tetrahydrofuran, and methyl 1-phenyl-allyl carbonate (38.6 mg, 0.201 mmol) were added successively. The reaction mixture was stirred at 65° C. for 8 h, poured into water and extracted with ethyl acetate. The combined organic layers were dried over sodium sulfate, and the solvent was removed under reduced pressure to give a mixture of branched products (the ratio of diastereomers was 1.2/1) and linear product. The ratio of methyl 2-acetyl-3-phenyl-pent-4-enoate and linear compound was determined to be 52.8/1 by $^1$H NMR (400 MHz). The residue was chromatographed on silica (1/8 ethyl acetate/petroleum ether, Rf=0.3) to yield the mixture of diastereomers and linear compound. (30.6 mg, 66%, 72% BRSM) [α]$_D$=+28.7° (c 1.21, CHCl$_3$)

Example 17

Reaction of Cinnamyl Diethyl Phosphate with Sodio Methyl Acetoacetate Using 20 mol % catalyst S, S-ligand I (19.4 mg, 0.060 mmol) and Mo(CO)$_3$(EtCN)$_3$ (13.8 mg, 0.04 mmol) were dissolved in 1.0 ml of tetrahydrofuran at rt., and the reaction mixture was heated at 60° C. for 1 h. After cooling to rt., a solution of sodio methyl acetoacetate in 1.0 ml of tetrahydrofuran, prepared from methyl acetoacetate (51.1 mg, 0.44 mmol) and sodium hydride (10. 1 mg, 0.40 mmol) in tetrahydrofurane and cinnamyl diethyl phosphate (54.2 mg, 0.201 mmol) were added successively. The reaction mixture was stirred at 65° C. for 4 h, poured into water and extracted with ethyl acetate. The combined organic layers were dried over sodium sulfate, and the solvent was removed under reduced pressure to give a mixture of branched products (diastereomeric ratio 1.2/1) and linear product. The ratio of methyl 2-acetyl-3-phenyl-pent-4-enoate and linear compound was determined to be 45.7/1 by $^1$H NMR (400 MHz). The residue was chromatographed on silica (1/8 ethyl acetate/petroleum ether, Rf=0.3) to yield a mixture of diastereomers and linear compound. (39.8 mg, 85%) [α]$_D$=+33.6° (c 1.38, CHCl$_3$).

Example 18

Methyl 2-(4-Methoxy-benzoyl)-3-phenyl-pent-4-en-1-one

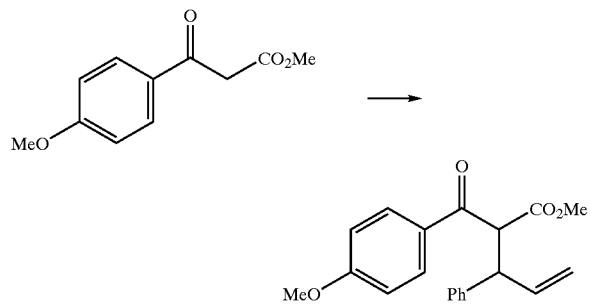

S, S-ligand I (9.7 mg, 0.030 mmol) and Mo(CO)$_3$(EtCN)$_3$ (6.9 mg, 0.020 mmol) were reacted with sodio methyl 4-methoxy-benzoacetate, prepared from methyl 4-methoxy-benzoacetate (92 mg, 0.44 mmol) and sodium hydride (10.1 mg, 0.40 mmol), cinnamyl diethyl phosphate (54.1 mg, 0.200 mmol) as described for Examples 16 and 17. The reaction yielded a mixture of branched products (diastereomeric ratio 1/1) and linear product. The ratio of methyl 2-(4-methoxy-benzoyl)-3-phenyl-pent-4-en-1-one and linear compound was determined to be 30.3/1 by $^1$H NMR (400 MHz). Purification gave 55.6 mg (86%); [α]$_D$=+65.8° (c 1.00, CHCl$_3$).

Examples 19A–B

Alkylation of 1-(2-Furyl)-2-propenyl Acetate with Dimethyl Sodioallylmalonate and Subsequent Diels-Alder Reaction A. A solution of Mo(CO)$_3$(EtCN)$_3$ (14.2 mg, 0.0411 mmol) and chiral ligand I (19.9 mg, 0.0613 mmol) in THF (2.0 mL) was stirred at 60° C. for 1 h. A solution of dimethyl sodjoallylmalonate, 3c (prepared from dimethyl allylmalonate (149 mg, 0.865 mmol) and 60% NaH (32.0 mg, 0.800 mmol) in THF (2.0 mL)) and 1-(2-furyl)-2-propenyl acetate, 2b (68.0 mg, 0.410 mmol) were successively added at room temperature. The mixture was stirred at room temperature for 12 h. Water (4 mL) was added to quench the reaction at room temperature. The mixture was extracted with diethyl ether (15 mL×3). The combined organic layer was washed with brine (10 mL×1) and dried (MgSO$_4$). The solvents were evaporated in vacuo, and the residue was purified by chromatography on silica gel (petroleum ether/ethyl acetate) to give the mixture of 4 and 5 (57.0 mg, 50% yield, 4:5=99:1).

B. The mixture of 4c and 5c (predominantly 4c) generated in Example 19A was stirred at 80° C. in ethanol-water (9.8 ml, 2:5) for 44 h. The mixture was cooled and extracted with diethyl ether (15 ml×3), and the combined organic layer was washed with brine (10 ml×1) and dried (MgSO$_4$). The solvents were evaporated in vacuo, and the residue was purified by chromatography on silica gel (petroleum ether/ethyl acetate=30/1–20/1–10/1) to give the mixture of 43 and 44 (44.4 mg, 79% yield (84% yield based on the recovered starting material), 43:44=76:24). The enantiomeric excesses were determined after isolating 43 and 44 by chromatography on silica gel (petroleum ether/ethyl acetate=30/1–20/1), respectively.

Diels-Alder Adduct 43 (major): $[\alpha]^{24.8}_D$=−1820 (c 2.09, CHCl$_3$). $^1$H NMR (300 MHz, CDCl$_3$): δ 6.38 (d, J=5.8 Hz, 1H), 6.29 (dd, J=5.8, 1.6 Hz, 1H), 5.73 (dt, J=17.1, 10.0 Hz, 1H), 5.25 (dd, J=17.1, 2.0 Hz, 1H), 5.15 (dd, J=10.0, 2.0 Hz, 1H), 5.04 (dd, J=4.4, 1.6 Hz, 1H), 4.02 (d, J=10.0 Hz, 1H), 3.76 (s, 3H), 3.66 (s, 3H), 2.45 (d, =5.8 Hz, 1H), 2.42 (d, J=2.5 Hz, 1H), 1.72–1.79 (m, 2H), 1.44 (dd, J=11.2, 8.2 Hz, 1H). $^{13}$C NMR (75 MHz, CDCl$_3$): δ 172.9, 169.8, 136.5, 136.4, 132.9, 118.8, 98.9, 80.1, 67.1, 52.9, 52.2, 49.3, 41.6, 38.9, 32.4. Diels-Alder Adduct 44 (minor): $[\alpha]^{26.0}_D$=−47.7° (c 0.57, CHCl$_3$). $^1$H NMR (300 MHz, CDCl$_3$): δ 6.28–6.32 (m, 2H), 5.69 (dt, J=17.0, 10.2 Hz, 1H), 5.34 (dd, J=17.0, 1.8 Hz, 1H), 5.23 (dd, J=10.2, 1.8 Hz, 1H), 4.98 (d, J=3.9 Hz, 1H), 3.90 (d, J=10.2 Hz, 1H), 3.74 (s, 3H), 3.67 (s, 3H), 2.88 (dd, J=13.7, 9.1 Hz, 1H), 2.20–2.27 (m, 1H), 2.06 (dd, J=13.7, 8.4 Hz, 1H), 1.70–1.76 (m, 1H), 1.54 (dd, J=11.5, 7.7 Hz, 1H). $^{13}$C NMR (75 MHz, CDCl$_3$): δ 171.8,171.0, 136.3, 134.3, 133.7, 119.8, 99.9, 79.7, 67.6, 52.7, 52.4, 51.2, 41.8, 38.0, 34.6.

Examples 20A–B

Preparation of Methyl(4E,6E)-2-methoxycarbonyl-2-[(1-phenyl)-2-propen-1-yl]-4,6-octadienoate 45 and Subsequent Diels-Alder Reaction

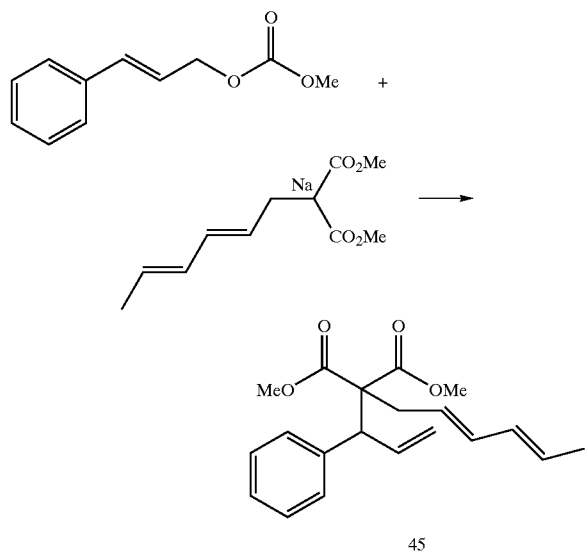

45

A. According to procedure B with Mo(CO)$_3$(EtCN)$_3$ (10,4 mg, 0.030 mmol) and ligand (R,R)-I (14.7 mg, 0.045 mmol) in 1.5 mL toluene and methyl cinnamyl carbonate (57.9 mg, 0.30 mmol), dimethyl (2E, 4E)-2,4-hexadienyl malonate [46] (140.7 mg, 0.66 mmol) and sodium hydride (24.1 mg, 0.61 mmol) in 1.5 mL THF. The reaction mixture was heated at 90° C. for 3 h. Work-up and flash chromatography (petroleum ether/ether 12:1) afforded 59.1 mg (60%) of the malonate adduct 45 as a colorless oil (isomeric purity >94:6; $^1$H NMR). $[\alpha]_D$=−2.0 (c 2.21, CH$_2$Cl$_2$). >94% ee.

B. Intramolecular Diels-Alder Reaction of Malonate 45:

A solution of malonate 45 (22.8 mg, 0.069 mmol) in 1 mL toluene was heated in a sealed tube at 150° C. for 48 h. The mixture was concentrated and the residue purified by flash chromatography (petroleum ether/ether 11:1) to afford 16.5 mg (72%) of a product tentatively identified as hydrindane 46, as a colorless oil consisting of a mixture of 3 stereoisomers in a ratio of 49:44:7 ($^1$H NMR; integration of the methoxycarbonyl signals). $[\alpha]_D$=+64.9 (c 0.45, CH$_2$Cl$_2$). $^1$H and $^{13}$C NMR of the two major isomers: $^1$H NMR (500 MHz, CDCl$_3$) δ: 7.19–7.33 (m, 10H), 5.81 (d, J=9.5 Hz, 1H), 5.75 (ddd, J=10.0, 6.5, 2.7 Hz, 1H), 5.57–5.65 (m, 2H), 3.95 (d, J=5.0 Hz, 1H), 3.81 (d, J=12.5 Hz, 1H), 3.78 (s, 3H), 3.73 (s, 3H), 3.22–3.31 (m, 1H), 3.09 (s, 3H), 3.03 (s, 3H), 2.81 (dd, J=13.3, 6.7 Hz, 1H), 2.36–2.56 (m, 4H), 2.02–2.18 (m, 3H), 1.84 (dt, J=13.0, 4.6 Hz, 1H), 1.78 (t, J=6.3 Hz, 1H), 1.52–1.61 (m, 1H), 1.44–1.49 (m, 1H), 1.01–1.13 (m, 1H), 1.05 (d, J=7.5 Hz, 3H), 0.99 (d, J=7.0 Hz, 3H). $^{13}$C NMR (75 MHz, CDCl$_3$): δ 173.48, 172.62, 171.1.6, 171.02, 141.91, 138.48, 134.34, 134.16, 128.85, 128.71, 127.96, 127.77, 127.19, 126.83, 126.64, 66.08, 65.46, 57.73, 54.84, 52.73, 52.62, 51.86, 51.66, 44.72, 42.10, 41.58, 39.30, 38.56, 35.92, 32.57, 30.47, 30.39, 21.98, 21.46. The 3rd isomer was identified by its two $^1$H NMR signals for the malonate methyl groups at 3.74 (s, 3H) and 3.10 (s, 3H).

Examples 21A–B

Preparation of Methyl (4E)-5-(1-Cyclohexen-1-yl)-2-methoxycarbonyl-2-(2-propenyl)-3-vinyl-4-pentenoate 47 and Subsequent Diels-Alder Reaction

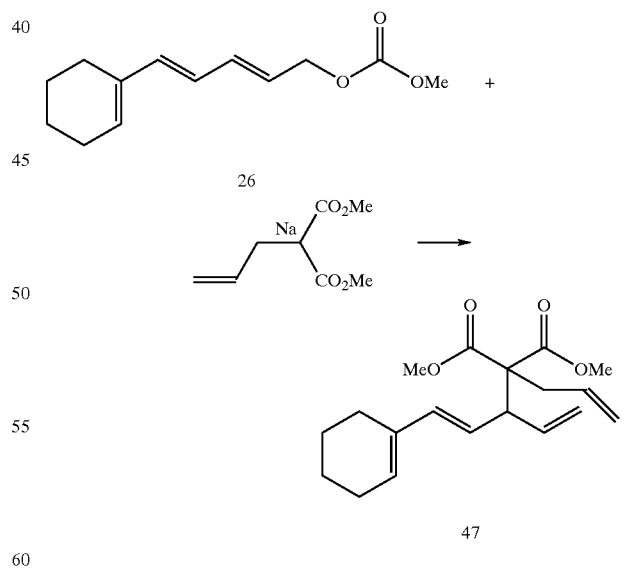

47

A. According to procedure B with Mo(CO)$_3$(EtCN)$_3$ (12.2 mg, 0.035 mmol) and ligand (R,R)-I (17.2 mg, 0.053 mmol) in 2 mL toluene and carbonate 26 (78.6 mg, 0.35 mmol), dimethyl allylmalonate (133.9 mg, 0.78 mmol) and sodium hydride (28.3 mg, 0.71 mmol) in 2 mL THF. The reaction mixture was heated at 90° C. for 2.5 h. Two isomers in a ratio of 5:1 were obtained, according to $^1$H NMR spectroscopy (integration of the methoxycarbonyl signals) of the crude mixture. Purification by flash chromatography (petroleum ether/ether 12:1) afforded 79.9 mg (71%) of pure 47 as a colorless oil. $[\alpha]_D=-52.0$ (c 0.38, $CH_2Cl_2$). The ee could not be determined.

B. Intramolecular Diels-Alder Reaction of Malonate 47:

A solution of malonate 47 (15.0 mg, 0.047 mmol) in 2 mL toluene was heated in a sealed tube at 150° C. for 15 h. The mixture was concentrated and the residue purified by flash chromatography (petroleum ether/ether 12:1) to afford 14.5 mg (97%) of a product tentatively identified as tricycle 63, as a colorless oil consisting of a mixture of 4 stereoisomers in a ratio of 3:3:1:1 ($^1$H NMR; integration of the methoxycarbonyl signals). $[\alpha]_D=-67.4$ (c 0.44, $CH_2Cl_2$). $^1$H NMR (300 MHz, $CDCl_3$) δ 4.95–5.77 (m, 4H), 3.75, 3.74, 3.73, 3.71, 3.67, 3.65, 3.62, 3.60 (8s, 6H), 2.68–3.07 (m, 1H), 0.80–2.54 (m, 15H). $^{13}$C NMR (75 MHz, $CDCl_3$) δ: 173.27, .172.96, 172.14, 171.89, 143.50, 141.57, 141.09, 137.32, 136.73, 135.97, 135.89, 135.39, 119.45, 119.28, 118.79, 118.63, 117.71, 117.53, 117.42, 63.85, 63.75, 54.92, 54.20, 53.96, 52.64, 52.63, 52.46, 52.10, 51.92, 47.49, 47.28, 42.91, 42.34, 40.35, 39.46, 39.22, 39.11, 39.00, 38.80, 38.67, 37.85, 37.23, 36.26, 36.16, 35.97, 35.16, 34.84, 34.79, 34.72, 34.30, 34.00, 29.69, 28.75, 28.51, 27.12, 27.04, 25.94.

Example 22

Synthesis of Ligand XIII

The amino group of (S)-phenylglycinol was protected as the benzyl carboxamate by reaction with benzyl chloroformate, and the hydroxy group was converted to the mesylate by reaction with mesyl chloride and triethylamine in dichloromethane. Reaction of the mesylate with $NaN_3$ in DMF gave the corresponding azide.

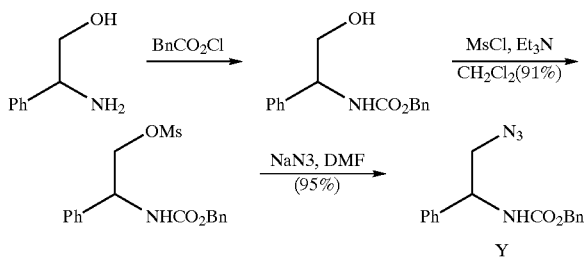

The azide was reduced to the diamine by catalytic hydrogenation, and reaction with picolinic acid yielded ligand XIII.

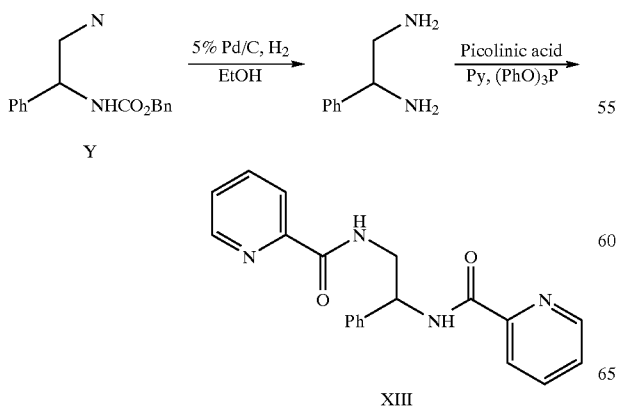

XIII

Example 23

Synthesis of (+)-(1S,2S)-Pyridine-2'-carboxylic Acid (2-Benzoylamino) Cyclohexyl Amide (Ligand XIV)

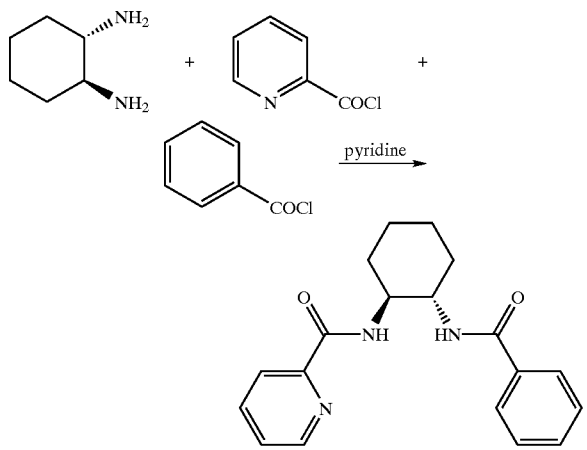

To a solution of picolinic acid (389 mg, 3.16 mmol) and pyridine (1.0 g, 12.6 mmol) in 10 mL of methylene chloride was added thionyl chloride (359 mg, 3.02 mmol) at −78° C. After stirring for 20 min, benzoyl chloride (383 mg, 2.73 mmol) and (S,S)-cyclohexyl diamine (328.2 mg, 2.87 mmol) were added successively. Then the reaction mixture was allowed to warm to room temperature. To the reaction mixture was added satd. sodium bicarbonate and then was extracted with methylene chloride (2×30 mL).

The combined organic layers were dried over sodium sulfate, and the solvent was removed under reduced pressure. The residue was chromatographed on silica (1/1 ethyl acetate/petroleum ether, Rf=0.3) to yield the ligand. (198.2 mg, 21%) $[\alpha]_D=+90.2°$ (c 0.54, $CHCl_3$); mp 202–203° C.; IR (neat): 3274, 2939, 2862, 1648, 1530, 1325, 996, 753, 696 cm$^1$; $^1$H NMR (300 MHz, $CDCl_3$) δ: 8.53 (d, J=4.6 Hz, 1H), 8.18 (s, 1H), 8.14 (d, J=7.8 Hz, 1H), 7.85–7.73 (m, 3H), 7.47–7.33 (m, 4H), 7.22 (m, 1H), 4.17–3.98 (m, 1H), 3.98–3.84 (m, 1H), 2.45–2.32 (m, 1H), 2.19–2.07 (m, 1H), 1.97–1.73 (m, 2H), 1.68–1.22 (m, 4H); $^{13}$C NMR (75 MHz, $CDCl_3$) δ: 167.1, 165.5, 149.2, 148.2, 137.3, 134.3, 131.1, 128.3 127.0, 126.3, 122.1, 56.3, 52.2, 32.4, 32.1, 25.0, 24.4; HRMS: Calc'd for $C_{19}H_{21}N_3O_2$: 323.1634, found: 0.323.1627.

Example 24

Synthesis of (1S,22)-(+)-N-(2'-Picolinoyl)-N'-(3'-picolinoyl)-1,2-trans-diaminocyclohexane (Ligand XV)

A. Synthesis of {2-[(Pbridine-2-carbonyl)-amino]-cyclohexyl}carbamic Acid tert-butyl Ester

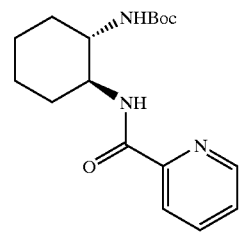

This intermediate was synthesized from mono Boc cyclohexyl diamine (Lagriffoule, *Chem. Eur. J.* 1997, 3, 912.)

(2.49 g, 11.6 mmol) and 2-picolinic acid (1.57 g, 12.8 mmol) by Vagg's method. (2.75 g, 74%).

$[\alpha]_D$=+25.70 (c 0.52, CHCl$_3$); mp 78–79° C.; IR (neat): 3346, 2935, 1705, 1664, 1528, 1365, 1174, 1014 cm$^{-1}$; $^1$H NMR (300 MHz, CDCl$_3$) δ: 8.56 (d, J=4.4 Hz, 1H), 8.27 (d, J=5.6 Hz, 1H), 8.17 (d, J=1H), 7.82 (ddd, J=1.5, 7.6, 7.6 Hz, 1H), 7.39 (dd, J=5.4, 6.6 Hz, 1H), 4.75 (d, J=8.8 Hz, 1H), 3.88–3.74 (m, 2H), 3.62–3.46 (m, 2H), 2.04 (m, 2H), 1.86–1.72 (m, 2H), 1.48–1.30 (m, 2H); $^{13}$C NMR (75 MHz, CDCl$_3$) δ; 164.6, 156.1, 149.7, 148.1, 137.0, 129.5, 125.9, 122.0, 79.0, 54.3, 54.1, 32.8, 32.5, 28.0, 24.9, 24.7; Anal: Calc'd for C$_{17}$H$_{25}$N$_3$O$_3$: C, 63.93; H, 7.89; N, 13.16. Found: C, 63.76; H, 7.78; N, 12.98.

B. (1S,2S)-(+)-N-(2-picolinoyl)-N'-(3-picolinoyl)-1,2-trans-diaminocycloheptane ligand XV)

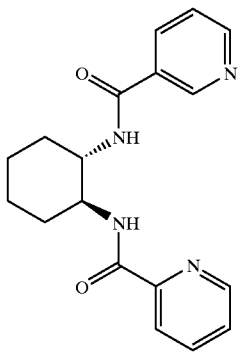

To {2-[(pyridine-2-carbonyl)-amino]-cyclohexyl}carbamnic acid tert-butyl ester, above (416 mg, 1.30 mmol), was added TFA at rt. After 1 h, the TFA was removed under reduced pressure. To the mixture was added 1N HCl (10 mL), and the solvent was removed under reduced pressure. To the residue were added triethyl amine (620 mg, 5.21 mmol), triphenyl phosphite (606 mg, 1.95 mmol), 3-picolinic acid (240 mg, 1.95 mmol) and pyridine (5 mL). The resulting mixture was heated at 100° C. for 15 h and then taken up with CHCl$_3$. The solution was washed with aq. NaHCO$_3$ which was extracted with CHCl$_3$ (2×30 mL). The combined organic layer was dried over Na$_2$SO$_4$, and the solvent was removed under reduced pressure. Purification by silica gel chromatography (EtOAc/hexane=1.5/1, Rf=0.3) yielded 274 mg (65%) of the ligand. $[\alpha]_D$=+70.10 (c 0.63, CHCl$_3$); mp 201–202° C.; IR (neat): 3439, 3338, 3270, 2938, 1655, 1535, 1326,712 cm$^{-1}$; $^1$H NMR (300 MHz, CDCl$_3$) δ: 9.00 (d,J=1.5Hz, 1H), 8.66 (dd, J=1.2, 4.6 Hz, 1H), 8.54 (d, J=4.6 Hz, 1H), 8.23–8.12 (m, 2H), 8.07 (d, J=8.1 Hz, 1H), 7.82 (ddd, J=1.5, 7.6, 7.8 Hz, 1H), 7.57 (d, J=6.1 Hz, 1H), 7.42 (ddd, J=1.5, 6.3,6.4 Hz, 1H), 7.31 (dd, J=4.9, 7.8 Hz, 1H); $^{13}$C NMR (75 MHz, CDCl$_3$) δ: 165.9, 165.2, 151.8, 149.0, 148.6, 148.2, 137.4, 134.7, 129.9, 126.5, 123.2, 122.2, 57.0, 52.2, 32.2, 32.0, 25.0, 24.2; HRMS. Calc'd for C$_{18}$H$_{20}$N$_4$O$_2$: 324.1586, found: 324.1584.

Example 25

Allylic Alkylation Using Ligand XIV

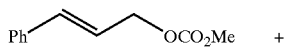

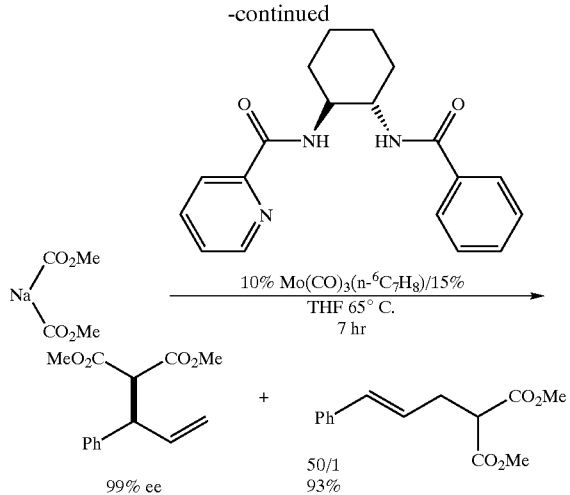

(S,S)-ligand XIV (9.7 mg, 0.03 mmol) and Mo(CO)$_3$(η$^3$-C$_7$H$_8$) (5.4 mg, 0.02 mmol) were dissolved in 1.0 mL of THF at rt, and the reaction mixture was heated at 60° C. for 30 min. After cooling to rt, a solution of sodio dimethyl molonate in 1.0 mL of THF (prepared from dimethyl malonate (58 mg, 0.44 mmol) and sodium hydride (10.1 mg, 0.40 mmol) in THF) and cinnamyl methyl carbonate (38.0 mg, 0.198 mmol) were added successively. The reaction mixture was stirred at 65° C. for 7 h, then poured into water and extracted with ether (2×30 mL). The combined organic layers were dried over magnesium sulfate, and the solvent was removed under reduced pressure. The residue was chromatographed on silica (1/10 ethyl acetate/petroleum ether, Rf=0.3) to yield a mixture of branched and linear compound. (45.5 mg, 93%) The ratio of branched and linear compound was determined to be 50/1 by $^1$H NMR (300 Mhz). (2×PhCH(CHE$_2$)CHCH$_2$/PhCHCHCH$_2$CHCHE$_2$) $[\alpha]_D$+35.1° (c 1.19, CHCl$_3$); 99% ee, HPLC (Daicel Chiralpak OJ, flow rate=1.0 mL/min, heptane/iPrOH=96/4, detection at 220 nm); $t_R$ 21.29 min (minor), $t_R$ 23.50 min (major).

Example 26

Allylic Alkylation Using Ligand XV

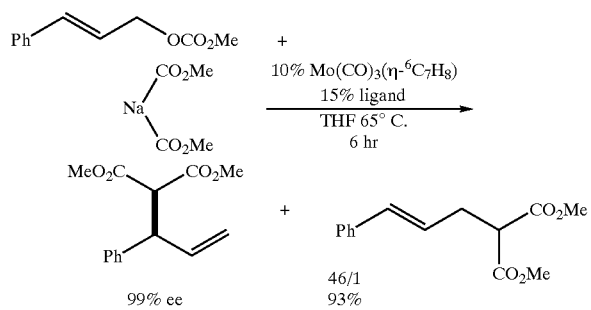

(S,S)-ligand XV (9.7 mg, 0.03 mmol) and Mo(CO)$_3$(η$^3$-C$_7$H$_8$) (5.4 mg, 0.02 mmol) were dissolved in 1.0 mL of THF at rt, and the reaction mixture was heated at 60° C. for 30 min and then cooled to rt. A solution of sodio dimethyl malonate in 1.0 mL of THF (prepared from dimethyl malonate (58 mg, 0.44 mmol) and sodium hydride (10.1 mg, 0.40 mmol) in THF) and cinnamyl methyl carbonate (38.6 mg, 0.201 mmol) were added successively. The reaction mixture was stirred at 65° C. for 6 h, then poured into water and extracted with ether (2×30 mL). The combined organic layers were dried over magnesium sulfate, and the solvent was removed under reduced pressure. The residue was chromatographed on silica (1/10 ethyl acetate/petroleum ether, Rf=0.3) to yield a mixture of branched and linear compound. (46.2 mg, 93%) The ratio of branched and linear compound was determined to be 46/1 by $^1$H NMR (300 Mhz). (2×PhC$\underline{H}$(CHE$_2$)CHCH$_2$/PhCHCHC$\underline{H}_2$CHCHE$_2$) 99% ee, HPLC (Daicel Chiralpak OJ, flow rate=1.0 mL/min, heptane/$^i$PrOH 96 4, detection at 220 nm); $t_R$ 19.61 min (minor), $t_R$ 22.25 min (major).

It is claimed:

1. A method of selective alkylation of an allyl group bearing a leaving group at an allylic position, said method comprising reacting a substrate containing said allyl group with an alkylating agent in the presence of a catalytic composition formed by contacting, in a suitable solvent, catalytic amounts of: (i) a chiral ligand L$^1$, and (ii) a soluble complex of a metal selected from the group consisting of molybdenum (0), tungsten (0), and chromium (0), having ligands which form a stable complex with the metal and are displaceable by ligand L under the conditions of said contacting, under conditions effective to produce an alkylated substrate which is enriched in one of the possible isomeric products of such alkylation, wherein said chiral ligand L$^1$ comprises:

a chiral component derived from a chiral diamine, said component comprising first and second carbon atoms, each bearing a binding group —NH—(C=O)—B, wherein said carbon atoms are connected by a direct bond or by a chain of one to three atoms comprising linkages selected from alkyl, alkyl ether, alkyl amino, and combinations thereof;

each group B is selected from alkyl, cycloalkyl, heterocycle, aryl, and aralkyl;

at least one group B is a N-heterocyclic or N-heteroaryl group CyN having an sp$^2$ hybridized ring nitrogen atom effective to coordinate to said metal atom; and at least one of said carbon atoms is a chiral carbon atom bearing a further substituent, wherein said substituent or substituents are independently selected from aryl, aralkyl, carbocycle, heterocycle, and secondary or tertiary alkyl having 3 or more carbons, and where substituents on adjacent chiral carbon atoms may together form a ring.

2. The method of claim 1, wherein said alkylation is enantioselective, and produces an alkylated substrate having an enantiomeric excess greater than 75%.

3. The method of claim 1, wherein said allyl group is nonsymmetrically substituted at its termini, and said alkylating is regioselective, such that said allyl group is alkylated predominantly at its more sterically hindered terminus.

4. The method of claim 1, wherein, in said ligand L$^1$, (i) each said group B is a group CyN as defined in claim 1, or (ii) each said carbon atom is a chiral carbon atom bearing a substituent as defined in claim 1; or (iii) both (i) and (ii) are present.

5. The method of claim 1, wherein at least one group B is a group CyN having an sp$^2$ hybridized ring nitrogen which is α to a ring carbon atom which is linked to the carbonyl (C=O) carbon of said binding group.

6. The method of claim 1, wherein said carbon atoms are connected by a direct bond.

7. The method of claim 6, wherein each said carbon atom is a chiral carbon atom bearing a substituent, and said substituents are independently aryl or together form a ring.

8. The method of claim 7, wherein said ring is a 5- to 7-membered carbocyclic ring, or a 5- to 7-membered heterocyclic ring having 1 to 3 ring atoms selected from oxygen, nitrogen and sulfur and,We remaining ring atoms carbon.

9. The method of claim 5, wherein said group or groups CyN are independently selected from 2-pyridyl, 2-quinolinyl, 1- or 3-isoquinolyl, 2- or 4-pyrimidyl, 2-triazinyl, 4-tetrazinyl, 2-pyrazinyl, 3- or 5-pyrazolyl, 3- or 5-triazolyl, 2-tetrazolyl, 2-oxazinyl, 2- or 5-oxazolyl, 2- or 5-thiazolyl, 2- or 4-imidazolyl, and dihydro derivatives of the above.

10. The method of claim 1, wherein neither terminus of said allyl group is aryl substituted.

11. The method of claim 1, wherein the alkylating agent is a stabilized carbanion of the form EE'RC$^-$M$^+$, where M$^+$ is a positively charged counterion, and each of E and E' is an electron-withdrawing substituent selected from keto, carboxylic ester, cyano, and sulfonyl, or an aromatic or heteroaromatic group capable of stabilizing an α-carbanion.

12. The method of claim 11, wherein at least one of E and E' is a carboxylic ester.

13. The method of claim 1, wherein said metal atom is molybdenum.

14. The method of claim 13, wherein said soluble molybdenum(0) complex bears ligands selected from the group consisting of CO, cycloheptatriene, lower alkyl nitrile, and lower alkyl isonitrile.

15. The method of claim 1, wherein the mole percent of said catalytic composition with respect to said substrate is from about 0.5% to about 15%.

* * * * *